(12) United States Patent
Strobel et al.

(10) Patent No.: US 8,299,102 B2
(45) Date of Patent: Oct. 30, 2012

(54) HETEROARYLCYCLOPROPANECARBOXA-MIDES AND THEIR USE AS PHARMACEUTICALS

(75) Inventors: Hartmut Strobel, Frankfurt am Main (DE); Paulus Wohlfart, Frankfurt am Main (DE); Gerhard Zoller, Schöneck (DE); David William Will, Frankfurt am Main (DE)

(73) Assignee: Sanofi, Paris (FR)

( * ) Notice: Subject to any disclaimer, the term of this patent is extended or adjusted under 35 U.S.C. 154(b) by 744 days.

(21) Appl. No.: 12/486,118

(22) Filed: Jun. 17, 2009

(65) Prior Publication Data
US 2010/0016278 A1    Jan. 21, 2010

Related U.S. Application Data

(63) Continuation of application No. PCT/EP2007/010708, filed on Dec. 8, 2007.

(30) Foreign Application Priority Data

Dec. 20, 2006  (EP) .................................... 06026396

(51) Int. Cl.
*C07D 211/70*     (2006.01)
*A61K 31/4418*    (2006.01)

(52) U.S. Cl. ........ 514/357; 514/362; 514/372; 514/374; 514/378; 514/396; 514/397; 514/438; 546/329; 548/196; 548/206; 548/215; 548/240; 548/300.1; 549/29

(58) Field of Classification Search .................. None
See application file for complete search history.

(56) References Cited

U.S. PATENT DOCUMENTS

| | | |
|---|---|---|
| 6,649,638 B1 | 11/2003 | Rehder et al. |
| 2005/0070588 A1 | 3/2005 | Weinstein et al. |

FOREIGN PATENT DOCUMENTS

| | | |
|---|---|---|
| EP | 0253502 | 1/1988 |
| EP | 0436199 | 7/1991 |
| WO | WO 93/21153 | 10/1993 |
| WO | WO 96/38141 | 12/1996 |
| WO | WO 99/47153 | 9/1999 |
| WO | WO 00/03746 | 1/2000 |
| WO | WO 01/81317 | 11/2001 |
| WO | WO 02/064146 | 8/2002 |
| WO | WO 02/064545 | 8/2002 |
| WO | WO 02/064546 | 8/2002 |
| WO | WO 02/064565 | 8/2002 |
| WO | WO 2004/014369 | 2/2004 |
| WO | WO 2004/014372 | 2/2004 |
| WO | WO 2004/014842 | 2/2004 |
| WO | WO 2004/016592 | 2/2004 |
| WO | WO 2004/050643 | 6/2004 |
| WO | WO 2004/094425 | 11/2004 |

OTHER PUBLICATIONS

U.S. Appl. No. 12/486,117, filed Jun. 17, 2009, Strobel et al.
U.S. Appl. No. 12/486,144, filed Jun. 17, 2009, Strobel et al.
Walker, et al., A Rationally Designed Universal Catalyst for Suzuki-Miyaura Coupling Processes, Angew. Chem. Int. Ed., (2004), vol. 43, pp. 1871-1876.
Corey, E. J., et al., Dimethyloxosulfonium Methylide ((CH3)2SOCH2) and Dimethylsulfonium Methylide ((CH3)2SCH2), Formation and Application to Organic Synthesis, Journal of the American Chemical Society, vol. 187, No. 6, (1955), 1353-1364.
Endres, M., et al., Stroke Protection by 3-Hydroxy-3-Methyiglutaryl (HMG)—CoA Reductase Inhibitors Mediated by Endothelial Nitric Oxide Synthase, Proc. Natl. Acad. Sci. USA, 95 (1998) 8880-8885.
Keshavarz-K., M., et al., An Improved Isolation of Triformytmethan (TFM): Properties and Preparation of Some Derivatives, Synthesis, (1988), pp. 641-645.
Kotha, S., et. al., Recent applications of the Suzuki-Miyaura cross-coupling reaction in organic synthesis, Tetrahedron 2002 (58) pp. 9633-9695.
Li, H., et al., Activation of Protein Kinase Ca and/or e Enhances Transcription of the Human Endothelial Nitric Oxide Synthase Gene, Molecular Pharmacology, vol. 53, pp. 630-637, (1998).
Miyaura, N., et al., Organobom Compounds, Topics in Current Chemistry, vol. 219, (2002), pp. 11-59.

(Continued)

*Primary Examiner* — Zinna Northington Davis
(74) *Attorney, Agent, or Firm* — Scully, Scott, Murphy & Presser, P.C.

(57) ABSTRACT

The present invention relates to heteroarylcyclopropanecarboxamides of the formula I,

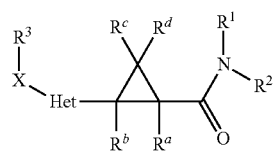

I in which Het, X, $R^a$, $R^b$, $R^c$, $R^d$, $R^1$, $R^2$ and $R^3$ have the meanings indicated in the claims, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

13 Claims, No Drawings

OTHER PUBLICATIONS

Moroi, M., et al., Interaction of Genetic Deficiency of Endothelial Nitric Oxide, Gender, and Pregnancy in Vascular Response to Injury, in Mice, The Journal of Clinical Investigation, 101, 6, (1998), 1225-1232.

Nakayama, et al., T-786-> C Mutation in the 5'-Flanking Region of the Endothelial Nitric Oxide Synthase Gene Is Associated With Coronary Spasm, Circulation 1999 (99) pp. 2864-2870.

Sessa, et al., Chronic Exercise in Dogs Increses Coronary Vascular Nitric Oxide Production and Endothelial Cell Nitric Oxide Synthase Gene Expression, Circ. Res., 1994 (74) 2, pp. 349-353.

Varenne, et al, Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries, Hum. Gene Ther. 2000 (11) pp. 1329-1339.

HETEROARYLCYCLOPROPANECARBOXA-MIDES AND THEIR USE AS PHARMACEUTICALS

CONTINUING DATA

This application is a CON of PCT/EP2007/01078 filed Dec. 8, 2007.

FIELD OF THE INVENTION

The present invention relates to heteroarylcyclopropanecarboxamides of the formula I,

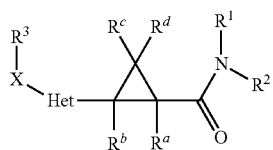

in which Het, X, $R^a$, $R^b$, $R^c$, $R^d$, $R^1$, $R^2$ and $R^3$ have the meanings indicated below, which modulate the transcription of endothelial nitric oxide (NO) synthase and are valuable pharmacologically active compounds. Specifically, the compounds of the formula I upregulate the expression of the enzyme endothelial NO synthase and can be applied in conditions in which an increased expression of said enzyme or an increased NO level or the normalization of a decreased NO level is desired. The invention further relates to processes for the preparation of compounds of the formula I, to pharmaceutical compositions comprising them, and to the use of compounds of the formula I for the manufacture of a medicament for the stimulation of the expression of endothelial NO synthase or for the treatment of various diseases including cardiovascular disorders such as atherosclerosis, thrombosis, coronary artery disease, hypertension and cardiac insufficiency, for example.

BACKGROUND OF THE INVENTION

Endothelial NO synthase (eNOS, NOS-III) belongs to a group of three isoenzymes which produce nitric oxide (nitrogen monoxide, NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349) were able to obtain a marked increase in eNOS by means of exercise training and the increase in shear stress associated therewith.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering, also in part to an increase in eNOS expression in vivo (Endres et al., Proc. Natl. Acad. Sci. USA 95 (1998) 8880). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. For the statins, as has already been mentioned, it has been possible to show such an increase in eNOS in vivo as a side effect. In view of the known range of side effects of this class of substances, however, it is unclear how far use of this effect can be made in a toxicologically unproblematic dose. Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension without, however, indicating a specific way of achieving this. Certain amide derivatives which upregulate the expression of endothelial NO synthase, in particular N-cycloalkyl amides in which the cycloalkyl ring is fused to a benzene ring or a heteroaromatic ring, have been described in WO 02/064146, WO 02/064545, WO 02/064546, WO 02/064565, WO 2004/014369, WO 2004/014372 and WO 2004/014842. Certain triaza- and tetraaza-anthracenedione derivatives which upregulate the expression of endothelial NO synthase have been described in WO 2004/094425. There still exists a need for further compounds which upregulate the expression of endothelial NO synthase and have a favorable property profile and are useful as pharmaceuticals for the treatment of various diseases such as atherosclerosis, coronary artery disease or cardiac insufficiency, for example. Surprisingly it has now been found that the compounds of the formula I are modulators of the transcription of endothelial NO synthase and in particular stimulate, or upregulate, the expression of eNOS, and are useful for the treatment of various diseases such as the mentioned cardiovascular disorders.

Certain heteroarylcyclopropanecarboxamides, in which an aryl or heteroaryl group is linked to the heteroaryl substituent on the cyclopropane ring and which are structurally related to formula I, have already been described. For example, in EP 0253502 N-disubstituted 2-heteroarylcyclopropanecarboxamides are generically disclosed which are intermediates for the preparation of fungicides and in which the heteroaryl group is an unsubstituted or substituted furanyl, thiophenyl or pyrrolyl group and the two substituents on the nitrogen atom of the amide group are $(C_1-C_4)$-alkyl or together with the nitrogen atom form an unsubstituted or substituted heterocyclic ring which optionally contains an additional heteroatom. In WO 2004/050643 inhibitors of HIV reverse transcriptase are described which comprise two (hetero)aryl groups and which can contain, among others, a cyclopropanecarboxamide moiety, for example the compound N-(2-nitrophenyl)-2-(1-(naphthalen-1-yl)-1-H-tetrazol-5-yl))-cyclopropanecarboxamide. In WO 96/374691-benzylindolyl derivatives, including the compound 3-(2-(1-(4-bromobenzyl)-5-methoxy-2-methyl-indol-3-yl)-cyclopropanecarbonyl)-4-isopropyl-2-oxazolidinone, are described which are inhibitors of cyclooxygenase 2 useful for the treatment of inflammatory diseases. In WO 93/21153 indole-2-carboxylic acid derivatives are described which are excitatory amino acid antagonists useful for the treatment of neurodegenerative diseases and other diseases, including the compounds 3-(2-phenylcarbamoyl-cyclopropyl)-4,6-dichloro-indole-2-carboxylic acid and the ethyl ester thereof. In EP 0436199 cyclopropyl derivatives are described which comprise an N-hydroxy moiety, for example an N-hydroxyurea or N-hydroxycarboxamide moiety, and which are lipoxygenase inhibitors useful for the treatment of inflammatory diseases, as well as respective compounds comprising an N-alkyloxy moiety, for example the compounds 2-(5-(4-fluorophenoxy)-furan-2-yl)-N-methoxy-N-methyl-cyclopropanecarboxamide and 2-(2-(4-chlorophenoxy)-thiazol-5-yl)-N-methoxy-N-methyl-cyclopropanecarboxamide. Also the imidazolyl derivatives described in US 2005/0070588, including the compound 2-(5-(4-methoxyphenyl)-2-phenyl-1H-imidazol-4-yl)-N-(4-pentyl-phenyl)-cyclopropanecarboxamide, are inhibitors of lipoxygenase. U.S. Pat. No. 6,649,638 and WO 2004/016592, which relate to inhibitors of protein prenylation useful for the treatment of cancer and other diseases, disclose the compound N-(1-carbamoyl-2-phenyl-ethyl)-2-(2-(3,4-dichlorophenyl)-5-(pyridin-3-yl)-2H-pyrazol-3-yl)-cyclopropanecarboxamide. In WO 96/38141 and WO 01/81317 imidazolylcyclopropanecarboxamides are disclosed which carry a triphenylmethyl group on the nitrogen atom of the imidazolyl ring and which are intermediates in the preparation of histamine $H_3$ receptor antagonists. However, the compounds specifically disclosed in these references are structurally distinguished from the compounds which are a subject of the present invention as compounds per se, and a stimulating effect of known heteroarylcyclopropanecarboxamides on the transcription or the expression of eNOS and their use in the treatment of diseases which is based on such effect, has not been described.

SUMMARY OF THE INVENTION

A subject of the present invention is a compound of the formula I,

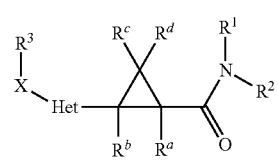

in which

Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond, $CH_2$, O and NH, provided that X cannot be O or NH if the group $R^3$—X— is bonded to a ring nitrogen atom of the group Het;

$R^a$, $R^b$, $R^c$ and $R^d$ are independently of each other chosen from hydrogen, fluorine and $(C_1-C_4)$-alkyl;

$R^1$ and $R^2$ are independently of each other chosen from hydrogen, $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl and heteroaryl groups can independently of each other be substituted on carbon atoms by one or more identical or different substituents $R^7$, or $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted on ring carbon atoms by one or more identical or different substituents $R^8$;

$R^3$ is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $H_2NSO_2$— and $(C_1-C_4)$-alkyl-$SO_2$—;

$R^4$ is chosen from hydrogen and $(C_1-C_4)$-alkyl;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di($(C_1-C_4)$-alkyl)amino, $((C_1-C_4)$-alkyl)-CONH—, di($(C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$ and $(C_1-C_4)$-alkyl-$SO_2$—;

$R^6$ is chosen from fluorine, OH, oxo, $(C_1-C_4)$-alkyloxy, $(C_1-C_4)$-alkylmercapto, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN and $CF_3$;

$R^7$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $SF_5$, $H_2NSO_2$— and $(C_1-C_4)$-alkyl-$SO_2$—;

$R^8$ is chosen from fluorine, $(C_1-C_4)$-alkyl, $(C_1-C_4)$-alkyloxy-$(C_1-C_2)$-alkyl-, OH, oxo, $(C_1-C_4)$-alkyloxy which can be substituted by one or more fluorine atoms, $(C_1-C_3)$-alkylenedioxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN and $CF_3$;

$R^9$ is chosen from hydrogen, $(C_1-C_4)$-alkyl, $((C_1-C_4)$-alkyl)-CO— and phenyl-CO—, wherein the phenyl group can be substituted by one or more identical or different substituents chosen from halogen, $(C_1-C_4)$-alkyl, $CF_3$ and $(C_1-C_4)$-alkyloxy;

$R^{10}$ is chosen from hydrogen and $(C_1-C_4)$-alkyl;

heteroaryl is a 5-membered or 6-membered, monocyclic aromatic group which contains one, two or three identical or different heteroatom ring members chosen from N, $NR^{10}$, O and S;

n is 0, 1 or 2, where all numbers n are independent of each other and can be identical or different;

in any of its stereoisomeric forms or a mixture of stereoisomeric forms in any ratio, or a physiologically acceptable salt thereof.

Another subject of the present invention is the use of a compound of the formula Ia

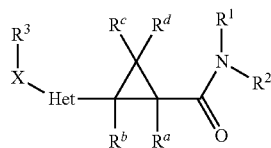

Ia in which

Het is 5-membered to 10-membered, monocyclic or bicyclic, aromatic group which contains one or more identical or different heteroatom ring members chosen from N, $NR^4$, O and S, and which can be substituted on ring carbon atoms by one or more identical or different substituents $R^5$;

X is chosen from a direct bond, $CH_2$, O, $CH_2$—O, O—$CH_2$, S, NH and N$((C_1-C_4)$-alkyl), or X is absent and in this case the phenyl, naphthalenyl or heteroaryl group representing the group $R^3$ is fused to the group Het, provided that X cannot be O, $CH_2$—O, S, NH or N$((C_1-C_4)$-alkyl) if the group $R^3$—X— is bonded to a ring nitrogen atom of the group Het;

$R^a$, $R^b$, $R^c$ and $R^d$ are independently of each other chosen from hydrogen, fluorine and $(C_1-C_4)$-alkyl;

$R^1$ and $R^2$ are independently of each other chosen from hydrogen, $(C_1-C_{10})$-alkyl, $(C_3-C_{10})$-alkenyl, $(C_3-C_{10})$-alkynyl, $(C_3-C_{10})$-cycloalkyl-$C_nH_{2n}$—, phenyl-$C_nH_{2n}$—, naphthalenyl-$C_nH_{2n}$— and heteroaryl-$C_nH_{2n}$—, wherein the groups $(C_1-C_{10})$-alkyl, $(C_3-C_{10})$-cycloalkyl, $(C_3-C_{10})$-alkenyl and $(C_3-C_{10})$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl, naphthalenyl and heteroaryl groups can independently of each other be substituted by one or more identical or different substituents $R^7$, or $R^1$ and $R^2$, together with the nitrogen atom carrying them, form a 4-membered to 10-membered, monocyclic or bicyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted by one or more identical or different substituents $R^8$;

$R^3$ is chosen from phenyl, naphthalenyl and heteroaryl which can all be substituted by one or more identical or different substituents chosen from halogen, $(C_1-C_6)$-alkyl, $(C_1-C_6)$-alkyloxy-$(C_1-C_3)$-alkyl-, OH, $(C_1-C_6)$-alkyloxy which can be substituted by one or more fluorine atoms, $(C_1-C_3)$-alkylenedioxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, $((C_1-C_6)$-alkyl)-$SO_2NH$—, di$((C_1-C_6)$-alkyl)aminocarbonyl-, $((C_1-C_6)$-alkyl)aminocarbonyl-, $((C_1-C_6)$-alkyloxy)carbonyl-, COOH, $CONH_2$, CN, $CF_3$, $((C_1-C_6)$-alkyl)$NHSO_2$—, di$((C_1-C_6)$-alkyl)$NSO_2$—, $H_2NSO_2$— and $(C_1-C_6)$-alkyl-$SO_2$—;

$R^4$ is chosen from hydrogen and $(C_1-C_4)$-alkyl;

$R^5$ is chosen from halogen, $(C_1-C_6)$-alkyl, $(C_1-C_6)$-alkyloxy-$(C_1-C_3)$-alkyl-, OH, $(C_1-C_6)$-alkyloxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, $((C_1-C_6)$-alkyl)-$SO_2NH$—, di$((C_1-C_6)$-alkyl)aminocarbonyl-, $((C_1-C_6)$-alkyl)aminocarbonyl-, $((C_1-C_6)$-alkyloxy)carbonyl-, COOH, $CONH_2$, CN, $CF_3$, $H_2NSO_2$—, $((C_1-C_6)$-alkyl)$NHSO_2$—, di$((C_1-C_6)$-alkyl)$NSO_2$— and $(C_1-C_6)$-alkyl-$SO_2$—;

$R^6$ is chosen from fluorine, OH, oxo, $(C_1-C_6)$-alkyloxy, $(C_1-C_6)$-alkylmercapto, di$((C_1-C_6)$-alkyl)amino, $((C_1-C_6)$-alkyl)-CONH—, $((C_1-C_6)$-alkyl)-$SO_2NH$—, di$((C_1-C_6)$-alkyl)aminocarbonyl-, $((C_1-C_6)$-alkyl)aminocarbonyl-, $((C_1-C_6)$-alkyloxy)carbonyl-, $CONH_2$, CN and $CF_3$;

$R^7$ is chosen from halogen, $(C_1-C_6)$-alkyl, $(C_1-C_6)$-alkyloxy-$(C_1-C_3)$-alkyl-, OH, $(C_1-C_6)$-alkyloxy which can be substituted by one or more fluorine atoms, $(C_1-C_3)$-alkylenedioxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, $((C_1-C_6)$-alkyl)-$SO_2NH$—, di$((C_1-C_6)$-alkyl)aminocarbonyl-, $((C_1-C_6)$-alkyl)aminocarbonyl-, $((C_1-C_6)$-alkyloxy)carbonyl-, $CONH_2$, CN, $CF_3$, $SF_5$, $H_2NSO_2$—, $((C_1-C_6)$-alkyl)$NHSO_2$—, di$((C_1-C_6)$-alkyl)$NSO_2$— and $(C_1-C_6)$-alkyl-$SO_2$—;

$R^8$ is chosen from halogen, $(C_1-C_6)$-alkyl, $(C_1-C_6)$-alkyloxy-$(C_1-C_3)$-alkyl-, OH, oxo, $(C_1-C_6)$-alkyloxy which can be substituted by one or more fluorine atoms, $(C_1-C_3)$-alkylenedioxy which can be substituted by one or more fluorine atoms, $(C_1-C_6)$-alkylmercapto, $NH_2$, $(C_1-C_6)$-alkylamino, di$((C_1-C_6)$-alkyl)amino, $((C_1-C_6)$-alkyl)-CONH—, $((C_1-C_6)$-alkyl)-$SO_2NH$—, di$((C_1-C_6)$-alkyl)aminocarbonyl-, $((C_1-C_6)$-alkyl)aminocarbonyl-, $((C_1-C_6)$-alkyloxy)carbonyl-, $CONH_2$, $CN$, $CF_3$, $H_2NSO_2$—, $((C_1-C_6)\text{-alkyl})NHSO_2$—, $di((C_1-C_6)\text{-alkyl})NSO_2$— and $(C_1-C_6)\text{-alkyl-SO}_2$—;

$R^9$ is chosen from hydrogen, $(C_1-C_6)$-alkyl, $((C_1-C_6)$-alkyl)-CO— and phenyl-CO—, wherein the phenyl group can be substituted by one or more identical or different substituents chosen from halogen, $(C_1-C_4)$-alkyl, $CF_3$ and $(C_1-C_4)$-alkyloxy;

$R^{10}$ is chosen from hydrogen and $(C_1-C_4)$-alkyl;

heteroaryl is a 5-membered to 10-membered, monocyclic or bicyclic aromatic group which contains one or more identical or different heteroatom ring members chosen from N, $NR^{10}$, O and S;

n is 0, 1, 2 or 3, where all numbers n are independent of each other and can be identical or different;

in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other disease mentioned above or below herein.

DETAILED DESCRIPTION OF THE INVENTION

If in the compounds of the formulae I and Ia any groups, substituents, heteroatom ring members, numbers or other features such as, for example, $R^4$, $R^5$, $R^6$, $R^7$, $R^8$, $R^9$, $R^{10}$, alkyl groups, the number n, etc. can occur several times, they can all independently of one another have any of the indicated meanings and can in each case be identical or different from one another. Similarly, in groups such as dialkylamino, for example, the alkyl groups can be identical or different.

Alkyl, alkenyl and alkynyl groups can be linear, i.e. straight-chain, or branched. This also applies when they are part of other groups, for example alkyloxy groups (=alkoxy groups, i.e. alkyl-O— groups), alkyloxycarbonyl groups or alkyl-substituted amino groups, or when they are substituted. Substituted alkyl, alkenyl and alkynyl groups can be substituted by one or more, for example one, two, three, four or five, identical or different substituents which can be located in any desired positions.

Examples of alkyl groups containing one, two, three, four, five, six, seven, eight, nine or ten carbon atoms are methyl, ethyl, propyl, butyl, pentyl, hexyl, heptyl, octyl, nonyl, and decyl and, more specifically, the n-isomer of each of these groups, isopropyl, isobutyl, isopentyl, sec-butyl, tert-butyl, neopentyl or 3,3-dimethylbutyl. Alkenyl groups and alkynyl groups containing three, four, five, six, seven, eight, nine or ten carbon atoms can contain one or more double bonds and/or triple bonds. Preferably they contain one double bond or one triple bond, respectively, which can be present in any desired position of the group. In one embodiment of the invention a carbon atom which is part of a double bond or triple bond is not directly bonded to a nitrogen atom. I.e., in this embodiment a double bond or triple bond is not present in the terminal position of the alkenyl or alkynyl group which is directly bonded to the nitrogen atom. Examples of alkenyl and alkynyl are prop-1-enyl, prop-2-enyl (=allyl), but-2-enyl, 2-methylprop-2-enyl, 3-methylbut-2-enyl, hex-3-enyl, hex-4-enyl, 4-methylhex-4-enyl, dec-3-enyl, dec-9-enyl, prop-2-ynyl (=propargyl), but-2-ynyl, but-3-ynyl, hex-4-ynyl or hex-5-ynyl.

As far as applicable, the preceding explanations regarding alkyl groups apply correspondingly to divalent alkyl groups, i.e. alkanediyl groups and alkylene groups, such as the methylene group —$CH_2$— and the polymethylene groups —$CH_2$—$CH_2$— and —$CH_2$—$CH_2$—$CH_2$— occurring in divalent alkylenedioxy groups such as —O—$CH_2$—O—, —O—$CH_2$—$CH_2$—O— or —O—$CH_2$—$CH_2$—$CH_2$—O—, and the groups $C_nH_{2n}$, which can also be linear or branched and/or can be substituted by one or more, for example one, two, three, four or five, identical or different substituents which can be located in any desired positions. In general, the number of substituents can of course not exceed the number of hydrogen atoms in the unsubstituted parent system which can be replaced with a substituent and can be only one or two in the case of a $CH_2$ group, for example. Examples of the group $C_nH_{2n}$, in which the number n is 1, 2, or 3, are —$CH_2$—, —$CH_2$—$CH_2$—, —$CH_2$—$CH_2$—$CH_2$—, —$CH(CH_3)$—, —$C(CH_3)_2$—, —$CH(CH_3)$—$CH_2$—, —$CH_2$—$CH(CH_3)$—. If the number n in the group $C_nH_{2n}$ is 0 (=zero), the two groups which are attached to the group $C_nH_{2n}$ are directly connected to one another via a single bond. Similarly, if the group X is a direct bond, the groups $R^3$ and Het are directly connected to one another via a single bond. The two free bonds of a divalent alkylenedioxy group can be connected to the same carbon atom or to different carbon atoms in the residual molecule, for example to two adjacent carbon atoms in an aromatic ring.

Examples of cycloalkyl groups are cyclopropyl, cyclobutyl, cyclopentyl, cyclohexyl, cycloheptyl, cyclooctyl, cyclononyl and cyclodecyl. Substituted cycloalkyl groups can be substituted by one or more, for example one, two, three, four or five, identical or different substituents which can be located in any desired positions. In general, besides any other specified substituents, all cycloalkyl groups in the compounds of the formulae I and Ia, specifically cycloalkyl groups in the groups $R^1$ and $R^2$, can also carry one or more, for example one, two, three, four or five, identical or different $(C_1-C_4)$-alkyl substituents, for example methyl substituents, which can be located in any desired positions. Examples of alkyl-substituted cycloalkyl groups are 4-methylcyclohexyl, 4-tert-butylcyclohexyl or 2,3-dimethylcyclopentyl.

If a group like phenyl, naphthalenyl and heteroaryl, including the group Het, which can be unsubstituted or substituted, is substituted by one or more substituents, in general it can carry one, two, three, four or five identical or different substituents, for example. The substituents can be located in any desired positions. Substituted heteroaryl groups can be substituted on ring carbon atoms and/or on suitable ring nitrogen atoms, i.e. on ring nitrogen atoms which in the parent ring system are capable of carrying a hydrogen atom or a substituent, where substituents on such substituted ring nitrogen atoms are in particular alkyl groups such as $(C_1-C_4)$-alkyl groups. Suitable ring nitrogen atoms, such as the ring nitrogen atoms in a pyridine ring or a quinoline ring, can also be present as N-oxides or as quaternary salts, the latter preferably having a counter-anion which is derived from a physiologically acceptable acid. In monosubstituted phenyl groups the substituent can be located in the 2-position, the 3-position or the 4-position. In a disubstituted phenyl group the substituents can be located in 2,3-position, 2,4-position, 2,5-position, 2,6-position, 3,4-position or 3,5-position. In trisubstituted phenyl groups the substituents can be located in 2,3,4-position, 2,3,5-position, 2,3,6-position, 2,4,5-position, 2,4,6-position or 3,4,5-position. Naphthalenyl (=naphthyl) can be naphthalen-1-yl or naphthalen-2-yl. In monosubstituted naphthalen-1-yl groups the substituent can be located in the 2-, 3-, 4-, 5-, 6-, 7- or 8-position, in monosubstituted naphthalen-2-yl groups the substituent can be located in the 1-, 3-, 4-, 5-, 6-, 7- or 8-position. In disubstituted naphthalenyl groups the substituents can likewise occur in any desired positions in the ring via which the naphthalenyl group is bonded to the residual molecule, and/or in the other ring.

Unless stated otherwise in the respective definitions, heteroaromatic groups including heteroaryl groups and the group Het are preferably 5-membered or 6-membered monocyclic aromatic heterocyclic groups or 9-membered or 10-membered bicyclic aromatic heterocyclic groups, where the bicyclic groups contain a 6-membered ring fused to a 5-membered ring or two fused 6-membered rings. In bicyclic heteroaryl groups one or both rings can be aromatic, and one or both rings can contain heteroatom ring members. Preferably heteroaryl groups and other heterocyclic groups contain one, two or three, for example one or two, identical or different heteroatom ring members. The heteroatom ring members in heteroaryl groups and other heterocyclic groups are generally chosen from ring heteroatoms such as nitrogen, oxygen and sulfur, it being possible for suitable ring nitrogen atoms to carry a hydrogen atom or a substituent, such as the groups $R^4$ and $R^{10}$, as is the case in 5-membered aromatic heterocycles such as pyrrole, pyrazole, imidazole or triazole, or in bicyclic aromatic heterocycles such as benzoimidazole, for example. A monocyclic heteroaryl group or group Het which contains a group $R^4$ or $R^{10}$ can contain only one group $R^4$ or $R^{10}$, respectively, and is 5-membered. The heteroatom ring members in heteroaryl groups and other heterocyclic groups can be located in any desired positions provided that the resulting heterocyclic system is known in the art and is stable and suitable as a subgroup in a drug substance. For example, it is generally preferred that two atoms from the series O and S are not present in adjacent ring positions.

Examples of parent heterocycles of heteroaryl groups and other heterocyclic groups including the group Het are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, 1,2,3-triazine, 1,2,4-triazine, 1,3,5-triazine, 1,2,4,5-tetrazine, indole, benzothiophene, benzofuran, 1,3-benzodioxole (=1,2-methylenedioxybenzene), 1,3-benzoxazole, 1,3-benzothiazole, benzoimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, acridine or pteridine. Heteroaryl groups, including heteroaryl groups representing $R^3$, and other heterocyclic groups can be bonded via any desired suitable ring carbon atom and, in the case of nitrogen heterocycles, via any suitable ring nitrogen atom. Preferably they are bonded via a ring carbon atom. For example, thiophenyl (=thienyl) can be thiophen-2-yl or thiophen-3-yl, pyridinyl (=pyridyl) can be pyridin-2-yl, pyridin-3-yl or pyridin-4-yl, imidazolyl can be, for example, 1H-imidazol-1-yl, 1H-imidazol-2-yl, 1H-imidazol-4-yl or 1H-imidazol-5-yl, quinolinyl (=quinolyl) can be quinolin-2-yl, quinolin-3-yl, quinolin-4-yl, quinolin-5-yl, quinolin-6-yl, quinolin-7-yl or quinolin-8-yl. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

As far as applicable, the preceding explanations regarding heteroaryl groups apply correspondingly to groups which can be regarded as divalent heteroaryl groups, i.e. heteroarylene groups, such as the group Het in formulae I and Ia. In general, a divalent heteroaryl group can be bonded to the adjacent groups via any two desired suitable ring atoms including ring carbon atoms and/or, in the case of nitrogen heterocycles, ring nitrogen atoms. Preferably they are bonded via any two ring carbon atoms, in particular in the case of the group Het. In the case of a divalent bicyclic heteroaryl group, the positions via which it is bonded to the adjacent groups can be located in the same ring or in different rings. In the case of a divalent group derived from furan or thiophene, for example, the adjacent groups can be bonded in 2,3-position, 2,4-position, 2,5-position or 3,4-position. A divalent group derived from thiazole can be thiazole-2,4-diyl, thiazole-2,5-diyl or thiazole-4,5-diyl. A divalent group derived from pyridine can be pyridine-2,3-diyl, pyridine-2,4-diyl, pyridine-2,5-diyl, pyridine-2,6-diyl, pyridine-3,4-diyl or pyridine-3,5-diyl. In the case of an unsymmetrical divalent group the present invention includes all positional isomers, i.e., in the case of a pyridine-2,5-diyl group, for example, it includes the compound in which the one adjacent group is present in the 2-position and the other adjacent group is present in the 5-position as well as the compound in which the one adjacent group is present in the 5-position and the other adjacent group is present in the 2-position. Depending on the ranking order of the adjacent groups in the nomenclature of the compound, in the name of a compound the numbers of the locations of the adjacent groups may differ from the ones indicated above and, for example, a pyridine-2,5-diyl group may be designated as a pyridine-3,6-diyl group.

As far as applicable, the above explanations also apply correspondingly to the aromatic heterocycle which is formed by fusion of the group $R^3$ to the group Het in case the group X is absent. In the respective compounds of the formula Ia the resulting polycyclic heteroaromatic group, which represents the $R^3$—X-Het-moiety, is a bicyclic or tricyclic or tetracyclic ring system, preferably a bicyclic or tricyclic ring system, for example a bicyclic ring system, and contains one or more, for example one, two, three or four, identical or different heteroatom ring members chosen from those which can be present in the groups Het and $R^3$. A phenyl or naphthalenyl or heteroaryl group representing $R^3$ can be fused to, or condensed to, the group Het via any suitable bond in $R^3$ and any suitable bond in the group Het, provided that the resulting polycyclic heteroaromatic group is known in the art and is stable and suitable as a subgroup in a drug substance and that in the resulting group at least the ring bonded to the cyclopropyl group can be an aromatic ring, i.e. contain six conjugated pi electrons in case of a 5-membered or 6-membered monocyclic ring. For example, if the group Het in a compound of the formula Ia is a pyridine ring, X is absent and $R^3$ is phenyl, the latter carbocyclic ring can be fused to the bond between positions 2 and 3 or the bond between positions 3 and 4 in the pyridine ring, and the resulting polycyclic heteroaromatic group representing the $R^3$—X-Het-moiety is a quinolinyl or isoquinolinyl group. If a naphthalenyl group representing $R^3$ is fused to a pyridine ring representing Het, the resulting polycyclic heteroaromatic group representing the $R^3$—X-Het-moiety is an aza-anthracenyl or aza-phenanthrenyl group. The polycyclic heteroaromatic which is present in case X is absent, can be bonded to the cyclopropyl group via any suitable ring atom, preferably a ring carbon atom, in an aromatic ring originating from the group Het, and can be substituted by substituents as outlined above for the groups $R^3$ and Het.

The heterocyclic ring which can be formed by $R^1$ and $R^2$ together with the nitrogen atom which carries them, can be 4-membered, 5-membered, 6-membered, 7-membered, 8-membered, 9-membered or 10-membered, and can be saturated, i.e. contain no double bond within the ring, or unsaturated, including partially unsaturated and aromatic, in particular partially unsaturated, and contain, for example, one, two, three or four double bonds within the ring, provided the respective ring system is known in the art and is stable and suitable as a subgroup in a drug substance.

Examples of residues of heterocyclic rings formed by $R^1$ and $R^2$ together with the nitrogen atom which carries them, are azetidin-1-yl, pyrrolidin-1-yl, 2,5-dihydro-1H-pyrrol-1-yl, piperidin-1-yl, 1,2,3,4-tetrahydropyridin-1-yl, 1,2,5,6-tetrahydropyridin-1-yl, azepan-1-yl, azocan-1-yl, azecan-1-yl, octahydrocyclopenta[b]pyrrol-1-yl, 2,3-dihydro-1H-indol-1-yl, octahydro-1H-indol-1-yl, 2,3-dihydro-1H-isoindol-2-yl, octahydro-1H-isoindol-2-yl, 1,2,3,4-tetrahydroquinolin-1-yl, decahydroquinolin-1-yl, 1,2,3,4-tetrahydroisoquinolin-2-yl, decahydroisoquinolin-2-yl, 4,5,6,7-tetrahydrothieno[3,2-c]pyridin-5-yl, pyrazolidin-1-yl, 4,5-dihydro-1H-imidazol-1-yl, imidazolidin-1-yl, 1,4,5,6-tetrahydropyrimidin-1-yl, hexahydropyrimidin-1-yl, piperazin-1-yl, [1,3]diazepan-1-yl, [1,4]diazepan-1-yl, oxazolidin-3-yl, [1,3]oxazinan-3-yl, morpholin-4-yl, [1,3]oxazepan-3-yl, [1,4]oxazepan-4-yl, thiazolidin-3-yl, [1,3]thiazinan-3-yl, thiomorpholin-4-yl, [1,3]thiazepan-3-yl, [1,4]thiazepan-4-yl. As applies to the ring which can be formed by $R^1$ and $R^2$ together with the nitrogen atom carrying them in general, all listed examples of heterocyclic groups can be unsubstituted or substituted as indicated above, for example by $R^8$. For example, they can be substituted on one or more, for example one, two or three, preferably one or two, more preferably one, ring carbon atoms by one or more, for example one, two, three or four, preferably one or two, identical or different substituents such as $(C_1-C_4)$-alkyl, for example methyl, and $(C_1-C_4)$-alkyloxycarbonyl, for example methoxycarbonyl, and/or on one or more ring nitrogen atoms by substituents such as $(C_1-C_4)$-alkyl, for example methyl, and $(C_1-C_4)$-alkyl-CO—, for example acetyl, which latter groups represent $R^9$. Besides that, as applies to the ring which can be formed by $R^1$ and $R^2$ together with the nitrogen atom carrying them in general, ring sulfur atoms in the listed heterocyclic groups can carry one or two oxo groups, i.e. doubly bonded oxygen atoms, and thus become SO or $SO_2$ groups, i.e. sulfoxide or sulfone groups or S-oxides or S,S-dioxides. For example, the sulfur atom in a thiomorpholin-4-yl group can carry one or two oxo groups, and besides the thiomorpholin-4-yl group also the groups 1-oxo-thiomorpholin-4-yl and 1,1-dioxo-thiomorpholin-4-yl can be present in a compound of the invention.

Halogen is fluorine, chlorine, bromine or iodine, preferably fluorine, chlorine or bromine, more preferably fluorine or chlorine.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group. Evidently, an oxo group cannot occur as a substituent on a carbon atom in an aromatic ring.

The present invention includes all stereoisomeric forms of the compounds of the formulae I and Ia and their salts. With respect to each chiral center, independently of any other chiral center, the compounds of formulae I and Ia can be present in S configuration or substantially in S configuration, or in R configuration or substantially in R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings, including the cyclopropane ring depicted in formulae I and Ia, the invention includes both the E form and Z form, or the cis form and the trans form, as well as mixtures of these forms in all ratios. In one embodiment of the invention the groups $R^3$—X-Het and CO—$NR^1R^2$ on the cyclopropane ring are present in trans configuration, or substantially in trans configuration, with respect to each other, which configuration also is the trans configuration when considering all four groups $R^3$—X-Het, CO—$NR^1R^2$, $R^a$ and $R^b$ except in case that one of the groups $R^a$ and $R^b$ is fluorine and the other is different from fluorine. In another embodiment of the invention the groups $R^3$—X-Het and CO—$NR^1R^2$ on the cyclopropane ring are present in cis configuration, or substantially in cis configuration, with respect to each other. If desired, the preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally a derivatization can be carried out before a separation of stereoisomers. The separation of a mixture of stereoisomers can be carried out at the stage of the compound of the formula I or Ia or at the stage of a starting material or an intermediate during the synthesis. The present invention also includes all tautomeric forms of the compounds of formulae I and Ia and their salts.

In case the compounds of the formulae I and Ia contain one or more acidic and/or basic groups, i.e. salt-forming groups, the invention also comprises their corresponding physiologically or toxicologically acceptable salts, i.e. non-toxic salts, in particular their pharmaceutically acceptable salts. Thus, the compounds of the formulae I and Ia which contain an acidic group can be present on such groups, and can be used according to the invention, for example, as alkali metal salts, alkaline earth metal salts or as ammonium salts. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formulae I and Ia which contain a basic group, i.e. a group which can be protonated, can be present on such groups, and can be used according to the invention, for example, in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, nicotinic acid, isonicotinic acid, citric acid, adipic acid, and other acids known to the person skilled in the art. If the compounds of the formulae I and Ia simultaneously contain acidic and basic groups in the molecule, the invention also includes, in addition to the salt forms mentioned, inner salts or betaines or zwitterions. The salts of the compounds of the formulae I and Ia can be obtained by customary methods which are known to the person skilled in the art like, for example, by contacting the compound of the formula I or Ia with an organic or inorganic acid or base in a solvent or diluent, or by anion exchange or cation exchange from another salt. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention furthermore includes all solvates of compounds of the formulae I and Ia, for example hydrates or adducts with alcohols, active metabolites of the compounds of the formulae I and Ia, and also prodrugs and derivatives of the compounds of the formulae I and Ia which in vitro may not necessarily exhibit pharmacological activity but which in vivo are converted into pharmacologically active compounds, for example esters or amides of carboxylic acid groups.

In the compounds of the formula Ia the divalent group Het is preferably defined as in the compounds of the formula I. More generally, one embodiment of the present invention relates to the use of a compound of the formula I, which is defined as above or below, in any of its stereoisomeric forms or a mixture of stereoisomeric forms in any ratio, or a physiologically acceptable salt thereof, for the manufacture of a medicament for the stimulation of the expression of endothelial NO synthase and for the treatment of a disease in which such a stimulation, or an increase in NO level, is desired, for example a cardiovascular disorder such as atherosclerosis, coronary artery disease or cardiac insufficiency or any other diseases mentioned above or below herein.

More preferably, the divalent group Het in the compounds of the formulae I and Ia is a divalent aromatic group of the formula II

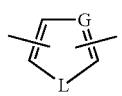

in which G is chosen from N and CH and L is chosen from S, O, NR$^4$, CH=CH, CH=N and N=CH, and which can be substituted by one or more identical or different substituents R$^5$, i.e. in which one or more ring carbon atoms can carry a substituent R$^5$ instead of the hydrogen atoms which are implicitly present on the carbon atoms depicted in formula II or which are specified in the definition of the groups G and L, with the proviso that the ring system depicted in formula II comprises at least one heteroatom ring member, i.e. a group NR$^4$ or an N, S or O atom, as a ring member. R$^5$ and R$^4$ in the ring system of the formula II are defined as indicated above with respect to the compounds of the formulae I and Ia. Particularly preferably the group Het in the compounds of the formulae I and Ia and the group of the formula II is chosen from the heteroarylene groups pyridinediyl, pyrimidinediyl, thiazolediyl, oxazolediyl, imidazolediyl, furandiyl and thiophenediyl, i.e. the divalent residues of pyridine, pyrimidine, thiazole, oxazole, imidazole, furan and thiophene, more particularly preferably from pyridinediyl, thiazolediyl, oxazolediyl, imidazolediyl and thiophenediyl, which can all be substituted by one or more identical or different substituents R$^5$ and wherein one of the ring nitrogen atoms of the imidazolediyl group, which represents the nitrogen atom in the group NR$^4$ in the definition of the group L, carries a group chosen from hydrogen and (C$_1$-C$_4$)-alkyl. In one embodiment of the invention Het is chosen from pyridinediyl, pyrimidinediyl, thiazolediyl, oxazolediyl, imidazolediyl and thiophenediyl, in another embodiment from pyridinediyl, thiazolediyl, imidazolediyl and thiophenediyl, in a further embodiment from pyridinediyl, thiazolediyl and thiophenediyl, which can all carry groups R$^4$ and R$^5$ as indicated. Especially preferably the group Het in the compounds of the formulae I and Ia and the group of the formula II is chosen from pyridinediyl and thiophenediyl, which can all be substituted by one or more identical or different substituents R$^5$. In one embodiment of the invention the group Het in the compounds of the formulae I and Ia and the group of the formula II is a pyridinediyl group which can be substituted by one or more identical or different substituents R$^5$.

In one embodiment of the present invention the groups representing the group Het in the compounds of the formulae I and Ia or the group of the formula II, in which latter group the bonds via which it is connected to the group R$^3$—X and the cyclopropyl group are represented by the lines intersecting the ring sides, are bonded to the group R$^3$—X and the cyclopropyl group via any two ring carbon atoms or via any one ring carbon atom and a suitable ring nitrogen atom, where in the latter case preferably the nitrogen atom is bonded to the group R$^3$—X and the carbon atom is bonded to the cyclopropyl group. In another embodiment of the invention the groups representing the group Het or the group of the formula II are bonded to the group R$^3$—X and the cyclopropyl group via any two ring carbon atoms. Preferably a pyridinediyl group representing Het or the group of the formula II is bonded to the adjacent groups via positions 3 and 6 of the pyridine ring, which positions may also be numbered as positions 5 and 2, respectively, depending on the ranking order of the groups bonded to the pyridine ring, or via positions 3 and 5, or via positions 2 and 6, particularly preferably via positions 3 and 6, where each of the group R$^3$—X and the cyclopropyl group can be present in each of the positions. I.e., in the latter pyridinediyl group, for example, which is bonded via positions 3 and 6, the group R$^3$—X can be present in position 3 and the cyclopropyl group in position 6, as well as the group R$^3$—X can be present in position 6 and the cyclopropyl group in position 3, where preferably the group R$^3$—X is present in position 6 and the cyclopropyl group in position 3. A pyrimidinediyl group representing the group Het or the group of the formula II is preferably bonded to the adjacent groups via positions 2 and 5, where each of the group R$^3$—X and the cyclopropyl group can be present in each of the positions and preferably the group R$^3$—X is present in position 2 and the cyclopropyl group is present in position 5. Preferably a group of the formula IIa,

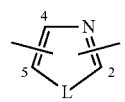

which represents Het or the group of the formula II and in which L is O, S or NR$^4$, i.e. which is an oxazolediyl, thiazolediyl or imidazolediyl group, is bonded to the adjacent groups via positions 2 and 5 or via positions 2 and 4, particularly preferably via positions 2 and 4, where each of the group R$^3$—X and the cyclopropyl group can be present in each of the positions and preferably the group R$^3$—X is present in position 4 and the cyclopropyl group in position 2. Preferably a thiophenediyl or a furandiyl group which represents Het or the group of the formula II is bonded to the adjacent groups via positions 2 and 5 or via positions 2 and 4, which latter positions may also be numbered as positions 5 and 3, particularly preferably via positions 2 and 4, where each of the group R$^3$—X and the cyclopropyl group can be present in each of the positions and preferably the group R³—X is present in position 4 and the cyclopropyl group in position 2.

Preferred groups Het or groups of the formula II thus include the divalent heteroaromatic groups depicted in the following formulae IIIa to IIIg which represent preferred embodiments of the structural moiety R³—X-Het- in the compounds of the formulae I and Ia, and in which the heteroaromatic group can be unsubstituted or substituted by one or more identical or different substituents R⁵. In formulae IIIa to IIIg the line starting at a ring carbon atom represents the free bond by which the group is bonded to the cyclopropyl group.

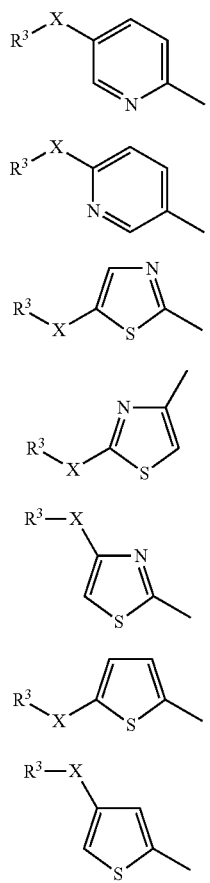

Particularly preferred groups Het or groups of the formula II include the divalent heteroaromatic groups depicted in the formulae IIIb, IIIe, IIIf and IIIg, especially the groups depicted in formulae IIIb and IIIg, more especially the group depicted in formula IIIb, which represent particularly and especially preferred embodiments of the structural moiety R³—X-Het- in the compounds of the formulae I and Ia.

In the group $CH_2$—O representing the group X, the $CH_2$ group is bonded to the group R³ and the oxygen atom is bonded to the group Het. In the group O—$CH_2$, the group $CH_2$ is bonded to the group Het and the oxygen atom is bonded to the group R³. In one embodiment of the invention, the group X in the compounds of the formula Ia is defined as in the compounds of the formula I. Preferably, the group X in the compounds of the formulae I and Ia is chosen from a direct bond, $CH_2$ and O, in particular from a direct bond and O, or in the compounds of the formula Ia the group X is absent and in this case the phenyl, naphthalenyl or heteroaryl group representing the group R³ is fused to the group Het, provided that X cannot be O if the group R³—X— is bonded to a ring nitrogen atom of the group Het. In one embodiment of the invention the group X in the compounds of the formulae I and Ia is chosen from a direct bond and O. In another embodiment of the present invention the group X in the compounds of the formulae I and Ia is a direct bond.

In a further embodiment of the present invention the group X in the compounds of the formula Ia is absent and in this embodiment the phenyl, naphthalenyl or heteroaryl group representing the group R³ is fused to the group Het. In still a further embodiment of the present invention the group X in the compounds of the formula Ia cannot be absent, i.e. In this embodiment the group X in the compounds of the formula Ia it is chosen from a direct bond, $CH_2$, O, $CH_2$—O, O—$CH_2$, S, NH and N((C₁-C₄)-alkyl) and preferably is defined as with respect to the compounds of the formula I.

In case the group X is absent, the phenyl, naphthalenyl or heteroaryl group representing the group R³ is fused to the group Het or the ring system depicted in formula II which contains the groups G and L. In case X is absent, in a particularly preferred embodiment of the present invention the structural moiety R³—X-Het- in the compounds of the formula Ia is a bicyclic heteroaryl group which comprises a monocyclic 5-membered or 6-membered heteroaromatic ring which represents the group Het and to which the cyclopropyl group is bonded, and a benzene ring which is fused to said heteroaromatic ring system and which represents the group R³, where the heteroaromatic ring can be substituted by one or more identical or different substituents R⁵ and the benzene ring can be substituted as indicated above with respect to R³. In case X is absent, the said structural moiety R³—X-Het- is more particularly preferably chosen from quinolinyl, isoquinolinyl, benzoimidazolyl, benzothiazolyl and benzothienyl, especially preferably from quinolinyl, benzoimidazolyl and benzothiazolyl, which are all bonded to the cyclopropyl group via the heterocyclic ring and which can be substituted as indicated.

Preferably, the groups $R^a$, $R^b$, $R^c$ and $R^d$ in the compounds of the formulae I and Ia are independently of each other chosen from hydrogen, fluorine and methyl. More preferably, $R^a$ and $R^b$ are independently of each other chosen from hydrogen and methyl. Particularly preferably, $R^a$ and $R^b$ are both hydrogen. In one embodiment of the invention, $R^c$ and $R^d$ are independently of each other chosen from hydrogen and methyl and, in particular, both are hydrogen. In another embodiment of the invention $R^c$ and $R^d$ both are hydrogen or both are fluorine and, in particular, both are hydrogen. In a further embodiment of the invention, $R^a$, $R^b$, $R^c$ and $R^d$ all are hydrogen.

If the ring which can be formed by the groups R¹ and R² together with the nitrogen atom carrying them is a monocyclic ring system, in one embodiment of the invention it is saturated or partially unsaturated. More specifically, in one embodiment the ring is saturated or contains one or two double bonds within the ring, and in another embodiment it is saturated or contains one double bond within the ring, and in a further embodiment it is saturated. If the said ring is a bicyclic ring system, in one embodiment the specific ring of the bicyclic ring system to which the CO group depicted in formula Ia is bonded, is saturated or is partially unsaturated, and in a more specific embodiment this ring contains one or two double bonds within the ring of which one double bond can be common to both rings, and the second ring of the bicyclic ring system is a saturated or an aromatic ring, in particular an aromatic ring such as a benzene ring. In the compounds of the formula Ia a monocyclic ring formed by the groups $R^1$ and $R^2$ together with the nitrogen atom carrying them preferably contains 4, 5, 6 or 7 ring members, and a bicyclic ring system preferably contains 9 or 10 ring members. The ring which can be formed by the groups $R^1$ and $R^2$ together with the nitrogen atom carrying them is preferably a monocyclic ring system.

In one embodiment of the present invention, the ring which can be formed by the groups $R^1$ and $R^2$ together with the nitrogen atom carrying them can contain, in addition to the said nitrogen atom carrying $R^1$ and $R^2$, one further heteroatom ring member, i.e. one further ring heteroatom or heteroatom group, which is chosen from N, $NR^9$, O, S, SO and $SO_2$ and preferably is chosen from N, $NR^9$, O and S and more preferably is chosen from $NR^9$, O and S. If the heterocycle formed by $R^1$ and $R^2$ together with the nitrogen atom carrying them is substituted by one or more identical or different substituents $R^8$, it preferably is substituted by one, two, three, four or five, more preferably by one, two, three or four, particularly preferably by one, two or three, more particularly preferably by one or two identical or different substituents $R^8$ on ring carbon atoms, in addition to oxo groups on ring sulfur atoms and/or groups $R^9$ on ring nitrogen atoms which may be present.

If $R^1$ and $R^2$, together with the nitrogen atom carrying them, form a ring, in one embodiment of the invention they form a saturated monocyclic 4-membered, 5-membered, 6-membered or 7-membered ring which, in addition to the nitrogen atom carrying $R^1$ and $R^2$, can contain one further heteroatom ring member group chosen from $NR^9$, O, S, SO and $SO_2$, preferably from $NR^9$, O and S, wherein the ring can be substituted by one or more identical or different substituents $R^8$. Examples of residues of such rings, from which the group —$NR^1R^2$ in the formulae I and Ia, which results if $R^1$ and $R^2$ together with the nitrogen atom carrying them form a ring, is preferably chosen, are azetidin-1-yl, pyrrolidin-1-yl, piperidin-1-yl, azepan-1-yl, imidazolidin-1-yl, hexahydropyrimidin-1-yl, piperazin-1-yl, [1,3]diazepan-1-yl, [1,4]diazepan-1-yl, oxazolidin-3-yl, [1,3]oxazinan-3-yl, morpholin-4-yl, [1,3]oxazepan-3-yl, [1,4]oxazepan-4-yl, thiazolidin-3-yl, [1,3]thiazinan-3-yl, thiomorpholin-4-yl, [1,3]thiazepan-3-yl and [1,4]thiazepan-4-yl. Preferred such residues include azetidin-1-yl, pyrrolidin-1-yl, piperidin-1-yl, azepan-1-yl, morpholin-4-yl, [1,4]oxazepan-4-yl, thiazolidin-3-yl and thiomorpholin-4-yl.

All rings formed by $R^1$ and $R^2$ together with the nitrogen atom carrying them can be substituted on carbon atoms by one or more identical or different substituents $R^8$, and/or can carry on a ring nitrogen atom which is not bonded to the CO group, which is depicted in formulae I and Ia, a group $R^9$, and/or can carry on a ring sulfur atom one or two oxo groups, to give a substituted group as indicated above. As examples of such substituted groups which are substituted by methyl, acetyl or methoxymethyl groups representing $R^8$ and/or $R^9$, and/or by an oxo group on a carbon atom representing $R^8$, and/or by one or two oxo groups on a sulfur atom, and which can represent the group —$NR^1R^2$ in formulae I and Ia, the groups 2-methoxymethyl-pyrrolidin-1-yl, 2,6-dimethyl-piperidin-1-yl, 2,6-dimethyl-morpholin-4-yl, 4-methyl-piperazin-1-yl, 4-acetyl-piperazin-1-yl, 3-oxo-piperazin-1-yl, 4-methyl-3-oxo-piperazin-1-yl, 1-oxo-thiomorpholin-4-yl and 1,1-dioxo-thiomorpholin-4-yl may be mentioned.

If $R^1$ and $R^2$ do not form a ring together with the nitrogen atom carrying them, they preferably are independently of each other chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, more preferably from $(C_1-C_4)$-alkyl, $(C_3-C_7)$-cycloalkyl, phenyl, phenyl-$CH_2$—, heteroaryl and heteroaryl-$CH_2$—, particularly preferably from $(C_1-C_4)$-alkyl, $(C_3-C_7)$-cycloalkyl, phenyl and heteroaryl, and in each case $R^2$ can in addition be hydrogen, wherein the groups $(C_1-C_4)$-alkyl and $(C_3-C_7)$-cycloalkyl can both be substituted by one or more identical or different substituents $R^6$, and the groups phenyl and heteroaryl can both be substituted by one or more identical or different substituents $R^7$. In one embodiment of the invention, in compounds in which $R^1$ and $R^2$ together with the nitrogen atom carrying them do not form a ring, $R^2$ is chosen from hydrogen and $(C_1-C_4)$-alkyl which can be substituted by one or more identical or different substituents $R^6$, and $R^1$ is defined as indicated. In another embodiment of the invention, in compounds in which $R^1$ and $R^2$ together with the nitrogen atom carrying them do not form a ring, $R^2$ is hydrogen and $R^1$ is defined as indicated. In a further embodiment of the invention, in compounds in which $R^1$ and $R^2$ together with the nitrogen atom carrying them do not form a ring, $R^1$ and $R^2$ are defined as indicated, but none of them can be hydrogen. If $R^1$ and/or $R^2$ is an alkenyl group or an alkynyl group, preferably the nitrogen atom carrying $R^1$ and $R^2$ is not in conjugation with a double bond or triple bond, i.e., preferably the nitrogen atom carrying $R^1$ and $R^2$ is not directly bonded to a carbon atom in an alkenyl group or alkynyl group which is part of a double bond or triple bond.

In the compounds of the formula Ia the groups $R^1$ and $R^2$ are preferably defined as in the compounds of the formula I. More preferably, the groups $R^1$ and $R^2$ in the compounds of the formulae I and Ia are independently of each other chosen from $(C_1-C_6)$-alkyl, $(C_3-C_6)$-alkenyl, $(C_3-C_6)$-alkynyl, $(C_3-C_7)$-cycloalkyl-$C_nH_{2n}$, phenyl-$C_nH_{2n}$— and heteroaryl-$C_nH_{2n}$—, and $R^2$ can in addition be hydrogen, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl groups and heteroaryl groups can be substituted by one or more identical or different substituents $R^7$, or $R^1$ and $R^2$, together with the nitrogen atom which carries them, form a 4-membered to 7-membered monocyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ and the nitrogen atom carrying them can be substituted by one or more identical or different substituents $R^8$.

Particularly preferably, the group $R^1$ in the compounds of the formulae I and Ia is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and the group $R^2$ is chosen from hydrogen, $(C_1-C_4)$-alkyl, $(C_3-C_7)$-cycloalkyl-$C_nH_{2n}$—, phenyl-$C_nH_{2n}$— and heteroaryl-$C_nH_{2n}$—, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, and wherein preferably the numbers n are independently of each other chosen from 0 and 1, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

More particularly preferably, the group $R^1$ in the compounds of the formulae I and Ia is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and the group $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, and wherein preferably the numbers n are independently of each other chosen from 0 and 1, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

Especially preferably, the group $R^1$ in the compounds of the formulae I and Ia is chosen from $(C_1-C_4)$-alkyl, $(C_3-C_7)$-cycloalkyl, phenyl and heteroaryl, and the group $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$.

In one embodiment of the invention, the groups $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring member chosen from N, $NR^9$, O, S, SO and $SO_2$, which can be identical or different, with the proviso that two ring members from the series O, S, SO and $SO_2$ cannot be present in adjacent ring positions, wherein the ring formed by $R^1$ and $R^2$ and the nitrogen atom carrying them can be substituted by one or more identical or different substituents $R^8$, and preferably $R^1$ and $R^2$, together with the nitrogen atom carrying them, form a 4-membered to 7-membered monocyclic saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$, and more preferred features of this embodiment are those outlined above.

In the compounds of the formula Ia the group $R^3$ is preferably chosen from phenyl, naphthalenyl and heteroaryl, more preferably from phenyl and heteroaryl, which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $((C_1-C_4)$-alkyl)-$SO_2NH$—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $H_2NSO_2$— and $(C_1-C_4)$-alkyl-$SO_2$—. Particularly preferably, the group $R^3$ in the compounds of the formula Ia is defined as in formula I. More particularly preferably, the group $R^3$ in the compounds of the formulae I and Ia is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—, and especially preferably by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $CF_3$ and $(C_1-C_4)$-alkyl-$SO_2$—, and more especially preferably by one or more identical or different substituents chosen from halogen, $(C_1-C_4)$-alkyl, $(C_1-C_4)$-alkyloxy which can be substituted by one or more fluorine atoms and $CF_3$. A heteroaryl group representing $R^3$ is preferably chosen from pyridinyl, pyrazolyl, thiophenyl and isoxazolyl, more preferably from pyridinyl and thiophenyl. A heteroaryl group representing $R^3$ is preferably bonded to the group X-Het via a ring carbon atom. In one embodiment of the invention the group $R^3$ is phenyl which can be substituted as indicated. In another embodiment of the invention the group $R^3$ is phenyl which is substituted as indicated. In a substituted group $R^3$ the number of substituents preferably is one, two, three, four or five, more preferably one, two, three or four, particularly preferably one, two or three, more particularly preferably one or two. In one embodiment of the present invention the group $R^3$ is a carbocyclic group, i.e. a phenyl group or a naphthalenyl group, and in another embodiment of the invention the group $R^3$ is a monocyclic group, i.e. a phenyl group or a monocyclic heteroaryl group, where all these groups can be substituted as indicated.

Preferably, the group $R^4$ in the compounds of the formulae I and Ia is chosen from hydrogen and methyl.

The group $R^5$ in the compounds of the formula Ia is preferably defined as in the compounds of the formula I. More preferably, the group $R^5$ in the compounds of the formulae I and Ia is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$alkyl)-CONH—, $CONH_2$, CN, $CF_3$ and $(C_1-C_4)$-alkyl-$SO_2$—. Particularly preferably the group $R^5$ in the compounds of the formulae I and Ia is chosen from halogen, $(C_1-C_4)$-alkyl, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, CN and $CF_3$, more particularly preferably from halogen, $(C_1-C_4)$-alkyl, $NH_2$ and $CF_3$, especially preferably from halogen and $(C_1-C_4)$-alkyl, for example from fluorine, chlorine and methyl. In one embodiment of the invention the group Het in the compounds of the formulae I and Ia is unsubstituted or substituted by one or more identical or different substituents which are chosen from fluorine, chlorine, methyl and $CF_3$, and preferably are chosen from fluorine, chlorine and methyl. In another embodiment of the invention the group Het in the compounds of the formulae I and Ia is unsubstituted. The number of substituents $R^5$, which are present on a substituted group Het, preferably is one, two, three or four, more preferably one, two or three, particularly preferably one or two, more particularly preferably one.

The group $R^6$ in the compounds of the formula Ia is preferably defined as in the compounds of the formula I. More preferably the group $R^6$ in the compounds of the formulae I and Ia is chosen from fluorine, $(C_1-C_4)$-alkyloxy, di$((C_1-C_4)$-alkyl)amino, $((C_1-C_4)$-alkyl)-CONH—, di$((C_1-C_4)$-alkyl) aminocarbonyl- and $CF_3$, more particularly preferably from fluorine and $(C_1-C_4)$-alkyloxy. Especially preferably, $R^6$ is fluorine. The number of substituents $R^6$ preferably is one, two or three, more preferably one or two, particularly preferably one.

The group $R^7$ in the compounds of the formula Ia is preferably defined as in the compounds of the formula I. More preferably the group $R^7$ in the compounds of the formulae I and Ia is chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—, particularly preferably from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—, more particularly preferably from halogen, $(C_1-C_4)$-alkyl, $(C_1-C_4)$-alkyloxy which can be substituted by one or more fluorine atoms, $((C_1-C_4)$-alkyl)-CONH—, $CONH_2$, CN and $CF_3$, especially preferably from halogen, $(C_1-C_4)$-alkyl, $(C_1-C_4)$-alkyloxy which can be substituted by one or more fluorine atoms, $((C_1-C_4)$-alkyl)-CONH—, $CONH_2$, CN and $CF_3$. The number of substituents $R^7$ preferably is one, two, three or four, more preferably one, two or three, particularly preferably one or two, for example one.

The group $R^8$ in the compounds of the formula Ia is preferably defined as in the compounds of the formula I. More preferably the group $R^8$ in the compounds of the formulae I and Ia is chosen from fluorine, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$ and $CF_3$, particularly preferably from fluorine, $(C_1-C_4)$-alkyl, $(C_1-C_4)$-alkyloxy-$(C_1-C_2)$-alkyl-, oxo, $((C_1-C_4)$-alkyloxy)carbonyl- and $CF_3$, more particularly preferably from fluorine, $(C_1-C_4)$-alkyl, and $(C_1-C_4)$-alkyloxy-$(C_1-C_2)$-alkyl-, where an oxo substituent representing $R^8$ can of course not be present in an aromatic ring in a ring system formed by $R^1$ and $R^2$ together with the nitrogen atom carrying them. The number of substituents $R^8$ preferably is one, two, three, four or five, more preferably one, two, three or four, particularly preferably one, two or three, more particularly preferably one or two, for example one.

The group $R^9$ in the compounds of the formula Ia is preferably defined as in the compounds of the formula I. More preferably the group $R^9$ in the compounds of the formulae I and Ia is chosen from hydrogen, $(C_1-C_4)$-alkyl and $((C_1-C_4)$-alkyl)-CO—, particularly preferably from hydrogen and $(C_1-C_4)$-alkyl.

Preferably, the group $R^{10}$ in the compounds of the formulae I and Ia is chosen from hydrogen and methyl.

In the compounds of the formula Ia a heteroaryl group is preferably defined as in the compounds of the formula I. Unless stated otherwise in the definition of any group containing a heteroaryl group, a heteroaryl group in the compounds of the formulae I and Ia is more preferably a 5-membered or 6-membered, monocyclic aromatic group which contains one or two identical or different heteroatom ring members chosen from N, $NR^{10}$, O and S. Aromatic heterocyclic residues which can represent heteroaryl occurring in the groups $R^1$, $R^2$ and $R^3$, for example, include pyridinyl, pyrimidinyl, thiophenyl, pyrazolyl, triazolyl, thiazolyl and isoxazolyl.

The number n in the compounds of the formula Ia is preferably defined as in the compounds of the formula I. More preferably the number n in the compounds of the formulae I and Ia is 0 or 1, wherein all numbers n are independent of each other and can be identical or different. An example of the group phenyl-$C_nH_{2n}$— in which the number n is 1 is the benzyl group (=phenyl-$CH_2$—). If a group $C_nH_{2n}$ is substituted by one or more substitutents, it is preferably substituted by one, two, three or four, more preferably by one, two or three, particularly preferably by one or two substituents, for example by one or two alkyl groups or by two fluorine atoms.

In preferred embodiments of the present invention one or more or all of the groups contained in the compounds of formulae I and Ia can independently of each other have any of the preferred definitions of the groups specified above or any one or some of the specific denotations which are comprised by the definitions of the groups and specified herein, all combinations of preferred definitions and/or specific denotations being a subject of the present invention. Also with respect to all preferred embodiments the invention includes the compounds of the formulae I and Ia in all their stereoisomeric forms and mixtures of stereoisomeric forms in all ratios, and their physiologically acceptable salts, as well as their tautomeric forms.

For example, one such embodiment relates to a compound and its use according to the present invention in which in formula I or formula Ia Het is chosen from pyridinediyl, thiazolediyl, oxazolediyl, imidazolediyl and thiophenediyl, which can all be substituted on ring carbon atoms by one or more identical or different substituents $R^5$ and in which one of the ring nitrogen atoms of the imidazolediyl group carries a group $R^4$ X is chosen from a direct bond and O;

$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

in any of its stereoisomeric forms or a mixture of stereoisomeric forms in any ratio, or a physiologically acceptable salt thereof.

Another such embodiment relates to a compound and its use according to the present invention in which in formula I or formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond and O, provided that X cannot be O if the group $R^3$—X— is bonded to a ring nitrogen atom of the group Het;

$R^a$ and $R^b$ are independently of each other chosen from hydrogen and $(C_1-C_4)$-alkyl;

$R^c$ and $R^d$ are independently of each other chosen from hydrogen and $(C_1-C_4)$-alkyl, or $R^c$ and $R^d$ both are fluorine;

$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen, $(C_1-C_4)$-alkyl, $(C_3-C_7)$-cycloalkyl- $C_nH_{2n}$—, phenyl-$C_nH_{2n}$— and heteroaryl-$C_nH_{2n}$—, wherein all ($C_1$-$C_4$)-alkyl and ($C_3$-$C_7$)-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is chosen from phenyl and heteroaryl which can all be substituted by one or more identical or different substituents chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—;

$R^4$ is chosen from hydrogen and ($C_1$-$C_4$)-alkyl;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—;

$R^6$ is chosen from fluorine, ($C_1$-$C_4$)-alkyloxy, di(($C_1$-$C_4$)-alkyl)amino, (($C_1$-$C_4$)-alkyl)-CONH—, di(($C_1$-$C_4$)-alkyl)aminocarbonyl- and $CF_3$;

$R^7$ is chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, ($C_1$-$C_2$)-alkylenedioxy which can be substituted by one or more fluorine atoms, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$, $SF_5$ and ($C_1$-$C_4$)-alkyl-$SO_2$—;

$R^8$ is chosen from fluorine, ($C_1$-$C_4$)-alkyl, ($C_1$-$C_4$)-alkyloxy-($C_1$-$C_2$)-alkyl-, OH, oxo, ($C_1$-$C_4$)-alkyloxy which can be substituted by one or more fluorine atoms, ($C_1$-$C_3$)-alkylenedioxy, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$, CN and $CF_3$;

$R^9$ is chosen from hydrogen, ($C_1$-$C_4$)-alkyl and (($C_1$-$C_4$)-alkyl)-CO—;

$R^{10}$ is chosen from hydrogen and ($C_1$-$C_4$)-alkyl;

heteroaryl is a 5-membered or 6-membered, monocyclic aromatic group which contains one, two or three identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

Another such embodiment relates to a compound and its use according to the present invention in which in formula I or formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is chosen from a direct bond and O, provided that X cannot be O if the group $R^3$—X— is bonded to a ring nitrogen atom of the group Het;

$R^a$ and $R^b$ are hydrogen;

$R^c$ and $R^d$ are independently of each other chosen from hydrogen and methyl;

$R^1$ is chosen from ($C_1$-$C_4$)-alkyl, ($C_3$-$C_7$)-cycloalkyl-$C_nH_{2n}$—, phenyl-$C_nH_{2n}$— and heteroaryl-$C_nH_{2n}$—, and $R^2$ is chosen from hydrogen and ($C_1$-$C_4$)-alkyl, wherein all ($C_1$-$C_4$)-alkyl and ($C_3$-$C_7$)-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is phenyl which can be substituted by one or more identical or different substituents chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, ($C_1$-$C_4$)-alkylmercapto, ($C_1$-$C_4$)-alkylamino, di(($C_1$-$C_4$)-alkyl)amino, $CONH_2$, CN, $CF_3$ and ($C_1$-$C_4$)-alkyl-$SO_2$—;

$R^4$ is chosen from hydrogen and ($C_1$-$C_4$)-alkyl;

$R^5$ is chosen from halogen, ($C_1$-$C_4$)-alkyl, ($C_1$-$C_4$)-alkyloxy-($C_1$-$C_2$)-alkyl-, OH, ($C_1$-$C_4$)-alkyloxy which can be substituted by one or more fluorine atoms, ($C_1$-$C_4$)-alkylmercapto, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$ and ($C_1$-$C_4$)-alkyl-$SO_2$—;

$R^6$ is chosen from fluorine and ($C_1$-$C_4$)-alkyloxy;

$R^7$ is chosen from halogen, ($C_1$-$C_4$)-alkyl, ($C_1$-$C_4$)-alkyloxy which can be substituted by one or more fluorine atoms, ($C_1$-$C_2$)-alkylenedioxy which can be substituted by one or more fluorine atoms, $NH_2$, ($C_1$-$C_4$)-alkylamino, di(($C_1$-$C_4$)-alkyl)amino, (($C_1$-$C_4$)-alkyl)-CONH—, $CONH_2$, CN, $CF_3$, $SF_5$ and ($C_1$-$C_4$)-alkyl-$SO_2$—;

$R^8$ is chosen from fluorine, ($C_1$-$C_4$)-alkyl, ($C_1$-$C_4$)-alkyloxy-($C_1$-$C_2$)-alkyl-, oxo, ($C_1$-$C_4$)-alkyloxy which can be substituted by one or more fluorine atoms, ($C_1$-$C_2$)-alkylenedioxy, (($C_1$-$C_4$)-alkyl)-CONH—, di(($C_1$-$C_4$)-alkyl)aminocarbonyl-, (($C_1$-$C_4$)-alkyl)aminocarbonyl-, (($C_1$-$C_4$)-alkyloxy)carbonyl-, $CONH_2$ and $CF_3$;

$R^9$ is chosen from hydrogen, ($C_1$-$C_4$)-alkyl and (($C_1$-$C_4$)-alkyl)-CO—;

$R^{10}$ is chosen from hydrogen and ($C_1$-$C_4$)-alkyl;

heteroaryl is a 5-membered or 6-membered, monocyclic aromatic group which contains one or two identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

Another such embodiment relates to the use of a compound according to the present invention in which in formula Ia Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;

X is absent and the phenyl group representing the group $R^3$ is fused to the group Het, $R^a$ and $R^b$ are hydrogen;

$R^c$ and $R^d$ are independently of each other chosen from hydrogen and methyl;

$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ together with the nitrogen atom carrying them can be substituted on ring carbon atoms by one or more identical or different substituents $R^8$;

$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;

$R^4$ is chosen from hydrogen and $(C_1-C_4)$-alkyl;

$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, $CONH_2$, CN, $CF_3$ and $(C_1-C_4)$-alkyl-$SO_2$—;

$R^6$ is chosen from fluorine and $(C_1-C_4)$-alkyloxy;

$R^7$ is chosen from halogen, $(C_1-C_4)$-alkyl, $(C_1-C_4)$-alkyloxy which can be substituted by one or more fluorine atoms, $(C_1-C_2)$-alkylenedioxy which can be substituted by one or more fluorine atoms, $NH_2$, $(C_1-C_4)$-alkylamino, di$((C_1-C_4)$-alkyl)amino, $((C_1-C_4)$-alkyl)-CONH—, $CONH_2$, CN, $CF_3$, $SF_5$ and $(C_1-C_4)$-alkyl-$SO_2$—;

$R^8$ is chosen from fluorine, $(C_1-C_4)$-alkyl, $(C_1-C_4)$-alkyloxy-$(C_1-C_2)$-alkyl-, oxo, $(C_1-C_4)$-alkyloxy which can be substituted by one or more fluorine atoms, $(C_1-C_2)$-alkylenedioxy, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$ and $CF_3$;

$R^9$ is chosen from hydrogen, $(C_1-C_4)$-alkyl and $((C_1-C_4)$-alkyl)-CO—;

$R^{10}$ is chosen from hydrogen and $(C_1-C_4)$-alkyl;

heteroaryl is a 5-membered or 6-membered, monocyclic aromatic group which contains one or two identical or different heteroatom ring members chosen from N, $NR^{10}$, O and S;

n is 0 or 1, where all numbers n are independent of each other and can be identical or different;

in any of its stereoisomeric forms or a mixture of stereoisomeric forms in any ratio, or a physiologically acceptable salt thereof.

As in any embodiment of the invention, in the preceding embodiments, which contain exemplary definitions of compounds according to the invention, one or more or all of the groups can have any of its preferred definitions specified above or any one or some of the specific denotations which are comprised by their definitions and are specified above.

A further embodiment of the present invention relates to any of the individual compounds of the formulae I and Ia and their use according to the invention which are specifically disclosed herein, including the compounds of all examples described below, in the form of the respective free compound as well as in the form of the physiologically acceptable salts thereof in general and, if a specific salt is disclosed herein, in the form of this specific salt, as well as to all tautomeric forms of the free compounds and their salts if tautomeric forms exist. I.e., this embodiment encompasses the physiologically acceptable salts in general of any individual compound specifically disclosed herein, irrespective thereof whether the compound is specifically disclosed as the free compound or as a specific salt. For example, as regards the compound {trans-2-[6-(2-chloro-phenoxy)-pyridin-3-yl]-cyclopropyl}-(piperidin-1-yl)-methanone, which is specifically disclosed as the free compound, subjects of the present invention are "{trans-2-[6-(2-chloro-phenoxy)-pyridin-3-yl]-cyclopropyl}-(piperidin-1-yl)-methanone" and "{trans-2-[6-(2-chloro-phenoxy)-pyridin-3-yl]-cyclopropyl}-(piperidin-1-yl)-methanone or a physiologically acceptable salt thereof". As regards the compound (azetidin-1-yl)-{trans-2-[6-(4-fluoro-phenyl)-pyridin-3-yl]-cyclopropyl}-methanone, for example, which is specifically disclosed as its trifluoroacetic acid salt, subjects of the present invention are "(azetidin-1-yl)-{trans-2-[6-(4-fluoro-phenyl)-pyridin-3-yl]-cyclopropyl}-methanone", "(azetidin-1-yl)-{trans-2-[6-(4-fluoro-phenyl)-pyridin-3-yl]-cyclopropyl}-methanone or a physiologically acceptable salt thereof" and "(azetidin-1-yl)-{trans-2-[6-(4-fluoro-phenyl)-pyridin-3-yl]-cyclopropyl}-methanone trifluoroacetic acid salt".

A further subject of the present invention are processes of preparation by which the compounds of the formulae I and Ia and salts thereof are obtainable and which are outlined in the following. There are several ways of preparing the compounds by assembling suitable building blocks. The synthetic strategies and the reaction types employed in these synthetic processes are per se known and are described in the literature, including the literature specifically referred to herein, and they can generally be performed under standard conditions which are familiar to one skilled in the art. In part, these processes comprise the reaction of a heteroarylcyclopropanecarboxylic acid or a derivative thereof of the formula IV with an amine of the formula V to give a compound of the formulae I or Ia, where the compound of the formulae IV and/or the compound of the formula V can also be employed, and/or the compound of the formula I or Ia can also be obtained, in the form of a salt.

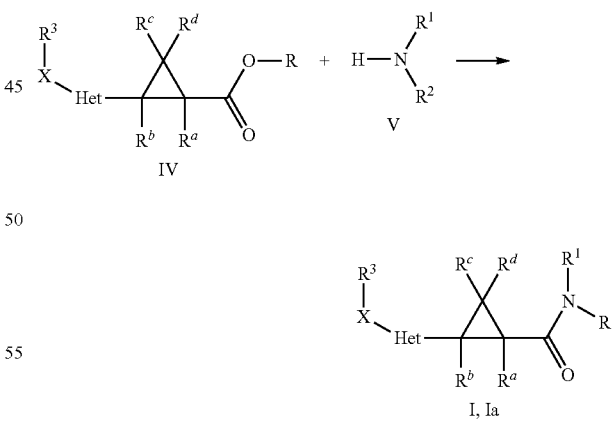

In the compounds of the formulae IV and V the groups Het, X, $R^a$, $R^b$, $R^c$, $R^d$, $R^1$, $R^2$ and $R^3$ are defined as in the compounds of the formulae I and Ia and, in addition, any functional groups can be present in protected form or in the form of precursor groups which are then converted into the desired final groups. As compounds of the formula IV, advantageously carboxylic acids or esters thereof such as an alkyl ester or benzyl ester can be employed, i.e. the group R in the compounds of the formula IV can be hydrogen or alkyl, for example ($C_1$-$C_4$)-alkyl like methyl or ethyl, or benzyl.

The reaction of a compound of the formula IV with a compound of the formula V to give a compound of the formula I or Ia can be performed under standard conditions for the conversion of a carboxylic acid or an ester thereof into a carboxamide or, from a different perspective, for the acylation of an amine by a carboxylic acid or an ester thereof. Compounds of the formula IV in which R is hydrogen, as well as compounds in which R is alkyl or benzyl, can be reacted with a compound of the formula V. If desired or more advantageous in a specific case, a compound of the formula IV in which COOR is a carboxylic acid group COOH can first be esterified and the obtained compound in which COOR is an ester group then reacted with a compound of the formula V. Likewise, a compound of the formula IV in which the group COOR is an ester group can first be cleaved to give the carboxylic acid, for example by acidic or basic saponification or by catalytic hydrogenation in the case of a benzyl ester, and the obtained compound in which COOR is a COOH group then reacted with a compound of the formula V. A compound of the formula IV in which COOR is an ester group, can be reacted with an amine of the formula V by combining the reactants at temperatures from about 20° C. to about 100° C. In a solvent, for example an ether like tetrahydrofuran (THF), dioxane, ethylene glycol dimethyl ether (1,2-dimethoxyethane, DME) or methyl tert-butyl ether (MTB), a hydrocarbon like dichloromethane, toluene or chlorobenzene, an alcohol like methanol, ethanol or isopropanol, an amide like dimethylformamide (DMF) or N-methylpyrrolidone (NMP), or another suitable solvent or a mixture of solvents. In the reaction of a compound of the formula IV in which the group COOR is a carboxylic acid group, preferably the latter group is first activated or converted into a reactive carboxylic acid derivative group. A suitable reactive carboxylic acid derivative is the carboxylic acid chloride, for example, which can be obtained by treatment of the acid with oxalyl chloride or thionyl chloride, for example. Suitable activating reagents for the carboxylic acid group include carbodiimides like N,N'-dicyclohexylcarbodiimide (DCC) or N,N'-diisopropylcarbodiimide (DIC), O-((cyano(ethoxycarbonyl)methylene)amino)-1,1,3,3-tetramethyluronium tetrafluoroborate (TOTU), N,N,N',N'-tetramethyl-O-(7-azabenzotriazol-1-yl)uronium hexafluorophosphate (HATU), propanephosphonic acid anhydride (PPA), N,N'-carbonyldiimidazole (CDI), and chloroformic acid alkyl esters like ethyl chloroformate or isobutyl chloroformate which latter reagents lead to the formation of mixed anhydrides. The acylation of a compound of the formula V with a compound of the formula IV in which the group COOR is a carboxylic acid group, is generally carried out in an inert solvent such as, for example, toluene, dichloromethane, THF, dioxane, DME, DMF or NMP, in the presence of a base such as, for example, an amine like triethylamine, ethyldiisopropylamine or N-ethylmorpholine (NEM), or a basic alkali metal compound like sodium carbonate, sodium hydrogencarbonate, potassium carbonate or sodium acetate, or in the presence of an excess of the amine of the formula V, at temperatures from about 0° C. to about 80° C.

Compounds of the formula IV can be obtained by different processes. According to one of them, a compound of the formula VI, i.e. a heteroarylacrylic acid derivative,

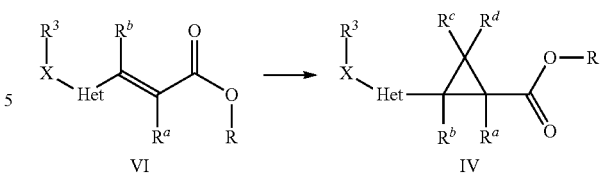

is subjected to a cyclopropanation reaction which results in the addition of the moiety $CR^cR^d$ to the double bond carrying the groups $R^a$ and $R^b$. In the compound of the formula VI the groups Het, X, $R^a$, $R^b$ and $R^3$ are defined as in the compounds of the formulae I and Ia and, in addition, any functional groups can be present in protected form or in the form of precursor groups which are then converted into the desired final groups. The group R in the compound of the formula VI is defined as in the compound of the formula IV, where in the compound of the formula VI as employed in the cyclopropanation reaction and in the compound of the formula IV as initially obtained the group COOR generally is an ester group, i.e., the group R is alkyl, for example ($C_1$-$C_4$)-alkyl like methyl or ethyl, or benzyl, and the formation of a compound of the formula IV in which R is hydrogen thus may include the cleavage of an ester group which may be performed in situ or in a separate step, for example by treatment with an acid or a base under standard conditions.

Cyclopropanation reagents, which can be used for converting a compound of the formula VI into a compound of the formula IV, generate a carbene or carbenoid that adds to the double bond. Such reagents include geminal diiodoalkanes, for example diiodomethane $CH_2I_2$ or 1,1-diiodoethane $CH_3$—$CHI_2$, in the presence of a zinc-copper couple or a zinc compound such as diethylzinc, for example the well know Simmons-Smith reagent, and diazoalkanes. The Simmons-Smith cyclopropanation, which is regarded as not involving a free carbene but a zinc carbenoid, can be performed in an inert solvent such as an ether, for example diethyl ether, or a chlorinated hydrocarbon, for example dichloromethane. Preferred cyclopropanation reagent are ylides, in particular sulfur ylides, which can be obtained from onium salts, in particular sulfonium salts, with a base. Examples of suitable sulfonium salts are trimethylsulfonium iodide $(CH_3)_3S^+I^-$ and trimethylsulfoxonium iodide $(CH_3)_2S(OCH_3)^+I^-$, which latter compound can also be named as trimethyloxosulfonium iodide, and the respective salts with other anions such as trimethylsulfoxonium chloride, which upon treatment with a strong base, for example an alkaline metal hydride, such as sodium hydride, or dimsyl sodium, i.e. the sodium salt of dimethyl sulfoxide which can in turn be obtained from dimethyl sulfoxide and sodium hydride, or an alkali metal hydroxide such as sodium hydroxide, optionally in the presence of a phase transfer catalyst such as a quaternary ammonium salt, provide dimethylsulfonium methylide and dimethylsulfoxonium methylide, respectively, which latter compound can also be named as dimethyloxosulfonium methylide (cf. Corey et al., J. Am. Chem Soc. 87 (1965) 1353). These sulfur ylides readily transfer a methylene group $CH_2$ onto a suitable double bond in a compound of the formula VI to give the respective cyclopropane derivative. A cyclopropanation reaction with a sulfonium salt is generally performed in an inert solvent, for example a hydrocarbon, such as toluene, or an ether, such as THF or dioxane, or dimethyl sulfoxide (DMSO) or a mixture of solvents, at temperatures from about −10° C. to about 70° C., in particular at temperatures from about 0° C. to about 30° C. such as at room temperature. Examples of cyclopropanation reagents which transfer a difluoromethylene group $CF_2$ onto a double bond to give a difluorocyclopropane, are sodium trifluoroacetate which is employed in the presence of azobisisobutyronitrile at temperatures up to about 180° C. In a solvent such as DMF, or trimethylsilyl 2-fluorosulfonyl-2,2-difluoroacetate which is employed in the presence of a fluoride such as sodium fluoride at temperatures up to about 120° C. In a solvent such as toluene.

Compounds of the formula VI can be obtained by condensing a compound of the formula VII, such as an aldehyde or a ketone, with a compound of the formula VII in a reaction such as a Knoevenagel reaction, a Wittig reaction or a Wittig-Horner reaction, for example, to provide a heteroarylacrylic acid or derivative thereof of the formula VI.

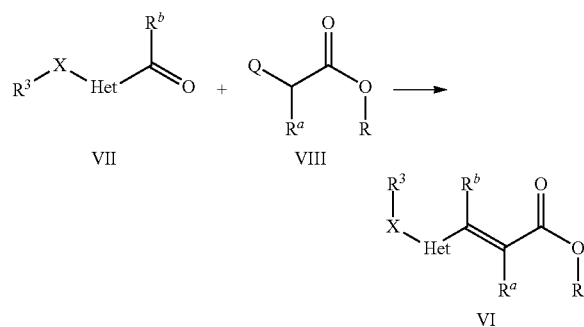

In the compounds of the formulae VII and VII the groups Het, X, $R^a$, $R^b$ and $R^3$ are defined as in the compounds of the formulae I and Ia and, in addition, any functional groups can be present in protected form or in the form of precursor groups which are then converted into the desired final groups. The group R in the compound of the formula VII is defined as in the compound of the formula IV. Depending on the reaction performed, the group Q in the compound of the formula VII can have different meanings. In case a Knoevenagel reaction is performed and $R^a$ denotes hydrogen, the compound of the formula VII can be malonic acid or a malonic acid derivative and the group Q can be a carboxylic acid group COOH or an ester group COOR in which R is $(C_1-C_4)$-alkyl or benzyl, for example. In such case the group COOR in the compound of the formula VII can, independently of the group Q, also be a carboxylic acid group COOH or an ester group like COO—$(C_1-C_4)$-alkyl. In the Knoevenagel reaction also cyanoacetic acid and cyanoacetic acid derivatives such as $(C_1-C_4)$-alkyl esters can be employed, and the group Q can be a cyano group in case of compounds in which $R^a$ is hydrogen. Unless malonic acid or a monoester thereof is employed in the Knoevenagel reaction, which generally react with decarboxylation and directly lead to the compound of the formula VI, the formation of a compound of the formula VI from compounds of the formulae VII and VII in a Knoevenagel reaction may include the hydrolysis of an ester group or cyano group which may be performed in situ or in a separate step.

In case a Wittig reaction or a Wittig-Horner reaction is performed, in which case the group COOR in the compounds of the formula VIII is an ester group and R is $(C_1-C_4)$-alkyl or benzyl, for example, the compound of the formula VIII can be a phosphonium salt, for example a $((C_1-C_4)$-alkyloxy)carbonylmethyltriphenylphosphonium halide which may carry an alkyl group representing $R^a$ on the methyl group, and the group Q then is a triphenylphosphonio group having a halide anion as counterion, or the compound of the formula VII can be a phosphonate, for example a di$((C_1-C_4)$-alkyl) $((C_1-C_4)$-alkyloxy)carbonylmethylphosphonate which may carry an alkyl group representing $R^a$ on the methyl group, and the group Q then is a di$((C_1-C_4)$-alkyl)phosphonyl group. Instead of employing a $((C_1-C_4)$-alkyloxy)carbonylmethyl-triphenylphosphonium halide and deprotonating it when performing the reaction, also a stable phosphorus ylide, for example a $((C_1-C_4)$-alkyloxy)carbonylmethylene-triphenylphosphane, can directly be employed in the reaction with the compound of the formula VII.

The above-discussed reactions of compounds of the formulae VII and VII to give compounds of the formula VI can generally be performed under standard conditions. For example, a Knoevenagel reaction with malonic acid or a malonic acid derivative can be performed by heating the reactants to temperatures from about 60° C. to about 120° C. In a solvent, for example a hydrocarbon like benzene, toluene or chlorobenzene, an alcohol like ethanol, or pyridine, preferably in the presence of a base such as an amine like piperidine, pyridine or β-alanine or an acid addition salt of an amine like ammonium acetate. Unless a stable phosphorus ylide is employed directly, a Wittig reaction or a Wittig-Horner reaction for providing a compound of the formula VI is generally performed under anhydrous conditions in a solvent, for example in an ether like THF, dioxane or DME or in an alcohol like ethanol, by first reacting the phosphonium salt or the phosphonate with a base, for example an alkali metal alcoholate like sodium methoxide or potassium tert-butoxide or an amide like lithium diisopropylamide or a hydride like sodium hydride or an organometallic compound like n-butyllithium, and then with a compound of the formula VII at temperatures from about −80° C. to about 100° C.

Heteroarylacrylic acid derivatives of the formula VI can be obtained from aldehydes or ketones of the formula VII also by means of various other reactions which are well-known in the art. As an example, the Perkin reaction may be mentioned which can be applied for preparing compounds of the formula VI in which $R^b$ is hydrogen, and in which the respective aldehyde of the formula VII is heated with an excess of a carboxylic acid anhydride, for example acetic anhydride in case a compound is prepared in which $R^a$ is hydrogen, to temperatures from about 100° C. to about 150° C. In the presence of an alkali metal salt of the carboxylic acid, for example sodium acetate or potassium acetate.

In another process, heteroarylacrylic acids or derivatives thereof of the formula VI can be obtained from compounds of the formula IX and acrylic acid derivatives of the formula X in a Heck reaction.

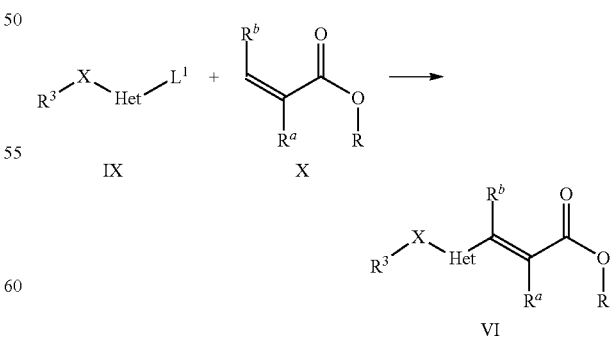

In the compounds of the formulae IX and X the groups Het, X, $R^a$, $R^b$ and $R^3$ are defined as in the compounds of the formulae I and Ia and, in addition, any functional groups can be present in protected form or in the form of precursor groups which are then converted into the desired final groups. The group COOR in the acrylic acid derivatives of the formula X preferably is an ester group and R is alkyl such as $(C_1\text{-}C_4)$-alkyl, like methyl or ethyl, or benzyl, for example. The group $L^1$ in the compounds of the formula IX is a leaving example, compounds of the formulae VII and IX may be obtained from appropriate starting compounds of the formulae XI and XIV, or the formulae XV and XVI, respectively, by reaction with appropriate compounds of the formulae XII and XIII.

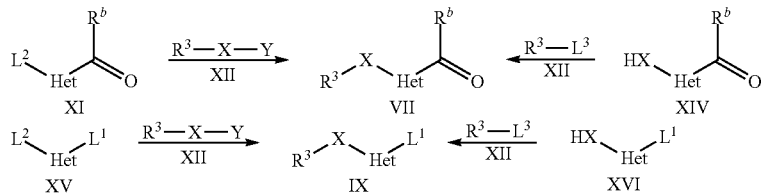

group which is substitutable by an alkene moiety under the conditions of the Heck reaction, such as halogen, for example chlorine, bromine or iodine, or a sulfonyloxy group, for example trifluoromethanesulfonyloxy. Generally, the reaction is performed in the presence of a transition metal catalyst, such as a palladium catalyst, for example palladium acetate in the presence of a phosphane like triphenylphosphane or tri(ortho-tolyl)phosphane, or bis(triphenylphosphane)palladium chloride or tetrakis(triphenylphosphane)palladium, and a base, such as an amine, for example a tertiary amine like triethylamine, or a basic alkali metal salt, for example potassium carbonate or sodium acetate, in an inert solvent, such as a hydrocarbon, for example toluene, chlorobenzene or dichloromethane, an ether, for example DME, THF or dioxane, an amide, for example DMF or NMP, a nitrile, for example acetonitrile, or a mixture of solvents, at temperatures from about 20° C. to about 110° C.

The compounds of the formulae VII, VIII, IX and X as well as the compounds of the formula V and other starting compounds which are employed in the processes for the preparation of intermediates and the final compounds of the formulae I and Ia discussed herein, are commercially available or can be prepared according to standard procedures described in the literature or in analogy to such procedures. For example, aldehydes and ketones of the formula VII can be obtained by such procedures from the parent heteroarenes of the formula $R^3$—X-Het-H or respective substituted heteroarenes which carry a substituent such as halogen, alkyl, carboxy, alkyloxycarbonyl or cyano, for example, by means of a reaction such as a Friedel-Crafts acylation, a Vilsmeier formylation, a metalation followed by reaction with a carboxylic acid derivative, a halogenation of an alkyl group followed by hydrolysis, an oxidation of an alkyl group, or a reduction or a reaction with an organometallic compound of a cyano or carboxy group or a derivative thereof. Compounds of the formula IX can be obtained, for example, from the parent heteroarenes or respective substituted heteroarenes which carry a substituent such as hydroxy or amino by means of a reaction such as a halogenation of the parent heteroarene or a hydroxy-substituted heteroarene group, a sulfonylation of a hydroxy group, or a diazotization of an amino group followed by reaction with halide.

The structural moiety $R^3$—X may already be present in the compounds of the formulae VII and IX which are available or may be obtained as outlined afore, or it may be introduced by standard procedures in starting compounds of the compounds of the formulae VII and IX or their starting compounds. For In the compounds of the formulae XI, XII, XIII, XIV, XV and XVI the groups Het, $R^b$ and $R^3$ are defined as in the compounds of the formulae I and Ia and, in addition, any functional groups can be present in protected form or in the form of precursor groups which are then converted into the desired final groups. When performing the contemplated processes, also the C=O group in the compounds of formulae XI and XIV, which is depicted in the formulae, can be present in protected form or in the form of a precursor group. The group X in the compounds of the formula XIV and XVI is chosen from O, O—$CH_2$, S, NH and N(($C_1$-$C_4$)-alkyl). The group X in the compound of the formula XII is chosen from a direct bond, $CH_2$, O, O—$CH_2$, $CH_2$—O, S, NH and N(($C_1$-$C_4$)-alkyl). In case the group X in the compound of the formula XII and the obtained compound of the formula VII or IX is O, $CH_2$—O, S, NH or N(($C_1$-$C_4$)-alkyl), the group Y in the compound of the formula XII is hydrogen. In case the group X in the compound of the formula XII and the obtained compound of the formula VII or IX is a direct bond, the group Y can be a boronic acid group or a derivative thereof, for example a boronic acid group —$B(OH)_2$, and the compound of the formula XII thus can be a boronic acid of the formula $R^3$—$B(OH)_2$. In case the group X in the compound of the formula XII is $CH_2$ or O—$CH_2$, the group Y can be a nucleophilically substitutable leaving group, for example halogen, in particular chlorine and bromine, or an arylsulfonyloxy or alkylsulfonyloxy group such as benzenesulfonyloxy, toluenesulfonyloxy, nitrobenzenesulfonyloxy, methanesulfonyloxy or trifluoromethanesulfonyloxy, and the compound of the formula XII thus can be an alkylating agent. The group $L^1$ in the compounds of formulae XV and XVI is defined as in the compound of the formula IX or can be present in the form of a precursor group which is then converted into the desired group $L^1$, for example a hydroxy group or a protected hydroxyl group which can be converted into a trifluoromethanesulfonyloxy leaving group by treatment with trifluoromethanesulfonyl chloride. The group $L^2$ in the compounds of formulae XI and XV is a leaving group which can be replaced with the group $R^3$—X— in a catalyzed or uncatalyzed nucleophilic aromatic substitution reaction or coupling reaction or a reaction of another type as it is performed when reacting the compounds of the formulae XI and XII or XV and XII. Examples of suitable leaving groups $L^2$ in the compounds of the formulae XI and XV are halogen, in particular chlorine, bromine and iodine, and sulfonyloxy groups such as trifluoromethanesulfonyloxy. The group $L^2$ in the compound of the formula XV can be identical to or different to the group $L^1$. If $L^1$ is a leaving group, the formation of the desired product of the formula IX in the reaction of the compounds of the formulae XV and XII can be achieved by applying suitable reaction conditions and employing a compound of the formula XV which contains two leaving groups $L^1$ and $L^2$ of different reactivity, or taking advantage of different reactivities of leaving groups which are present in different positions of the group Het in case $L^1$ and $L^2$ are identical. The latter situation applies to a compound of the formula XV such as 2,5-dibromopyridine, for example, in which the bromine atom in the 2-position is more reactive than the bromine atom in the 5-position. The group $L^3$ in the compound of the formula XIII likewise is a nucleophilically substitutable leaving group and can be halogen, in particular chlorine, bromine and iodine, or a sulfonyloxy group like trifluoromethanesulfonyloxy, for example.

The reactions of the compounds of the formulae XI and XV with a compound of the formula XII and of the compounds of the formulae XIV and XVI with a compound of the formula XII are generally performed in the presence of a base which binds the liberated acid of the formula $L^2$-H or $L^3$-H and/or enhances the nucleophilicity of compounds of the formulae XII, XIV and XVI which are alcohols, thiols or amines. Suitable bases include amines, for example tertiary amines like triethylamine, ethyldiisopropylamine, pyridine, amide salts, for example sodium amide or lithium diisopropylamide, organometallic compounds, for example organolithium compounds like n-butyllithium, alkali metal or alkaline earth metal hydrides, for example lithium hydride, sodium hydride or calcium hydride, alkali metal or alkaline earth metal hydroxides or quaternary ammonium hydroxides, for example lithium hydroxide, sodium hydroxide, potassium hydroxide, calcium hydroxide, benzyltrimethyl-ammonium hydroxide, alkali metal or alkaline earth metal alkoxides, for example sodium methoxide, sodium ethoxide, potassium methoxide, potassium ethoxide, potassium tert-butoxide, or other basic alkaline metal or alkaline earth metal compounds, for example carbonates like sodium carbonate, potassium carbonate, cesium carbonate, hydrogencarbonates like sodium hydrogencarbonate, potassium hydrogencarbonate, or other basic salts, or a mixture of bases. By means of the base, the compounds of the formula XII, XIV and XVI, which are alcohols, thiols or amines, can initially be converted into their corresponding salts. The reactions, which are nucleophilic arylation reactions and which can be performed in the presence or absence of a catalyst such as transition metal compound, are usually carried out in an inert solvent, such as a hydrocarbon or chlorinated hydrocarbon, for example n-heptane, toluene, xylene, chlorobenzene, dichloromethane, an ether, for example diethyl ether, diisopropyl ether, DME, THF, dioxane, an ester, for example ethyl acetate, butyl acetate, an amide, for example DMF, NMP, a nitrile, for example acetonitrile, an alcohol, for example methanol, ethanol, isopropanol, n-butanol, or another solvent, for example pyridine or DMSO, or a mixture of solvents. The reactions are generally performed at temperatures from about −20° C. to about 130° C.

In case the group X is a direct bond and the group Y in the compound of the formula XII is a boronic acid group —B(OH)$_2$ or a derivative thereof, the reaction of the compound of the formula XII with a compound of the formula XI or XV to give a compound of the formula VII or IX, in which X is a direct bond, can be carried out under the conditions of the well known Suzuki coupling, or Suzuki-Miyaura coupling, in the presence of a transition metal catalyst in an aqueous or non-aqueous solvent, for example a mixture of an ether such as DME and water. Suitable catalysts include palladium catalysts, for example tetrakis(triphenylphosphane) palladium or palladium acetate. Details on such coupling reactions of boronic acid derivatives, which can advantageously be used also in other processes for the preparation of the compounds of the invention, and intermediates therefor are explained in Kotha et al., Tetrahedron 58 (2002) 9633; Miyaura, Topics in Current Chemistry 219 (2002) 11; or Walker et al., Angew. Chem. Ind. Ed. 43 (2004) 1871, for example. If the group X is $CH_2$ or O—$CH_2$ and the compound of the formula XII is an alkylating agent as specified above, the reaction of a compound of the formula XII with a compound of the formula XI or XV to give a compound of the formula VII or IX, in which X is $CH_2$ or O—$CH_2$, can be carried out by metalating the compound of the formulae XI or XV, for example by means of an organolithium compound such as n-butyllithium, and then alkylating it with the compound of the formula XII or reacting it with an aldehyde of the formula $R^3$—CHO to give a compound containing the group $R^3$—CH(OH)— which is then reduced to the group $R^3$—$CH_2$—. An $R^3$—$CH_2$— group representing the group $R^3$—X— can also be introduced into a compound of the invention by performing an acylation reaction with a suitable starting compound to give a compound which contains the group $R^3$—CO— and reducing this group to the group $R^3$—$CH_2$—. As is usual and applies to all reactions performed in the synthesis of a compound of the invention, the detailed conditions of a specific preparation, including the solvent, the base, the temperature, the order of addition, the molar ratios and other parameters, are routinely chosen by the skilled person in view of the characteristics of the starting compounds and the target compound.

The order in which the structural moieties in a compound of the invention are introduced to give the final compound of the formula I or Ia, is variable and can be adapted to the needs and desire in a specific case. For example, besides by the processes for the preparation of the intermediates of the formula VI outlined above in which the group $R^3$—X— is present in the starting compounds of the formulae VII and IX which are reacted with the compounds of the formulae VII and X, respectively, just so the starting compounds of the formulae XI and VII, or the starting compounds of the formulae XV and X, may be reacted to give the intermediate of the formula XVII which does not yet contain the group $R^3$—X— and in which this group is introduced by reaction with a compound of the formula XII to give a compound of the formula VI.

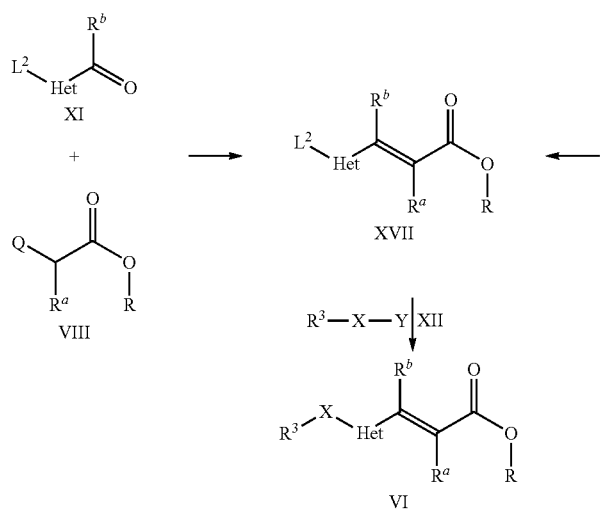

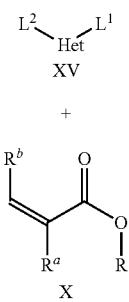

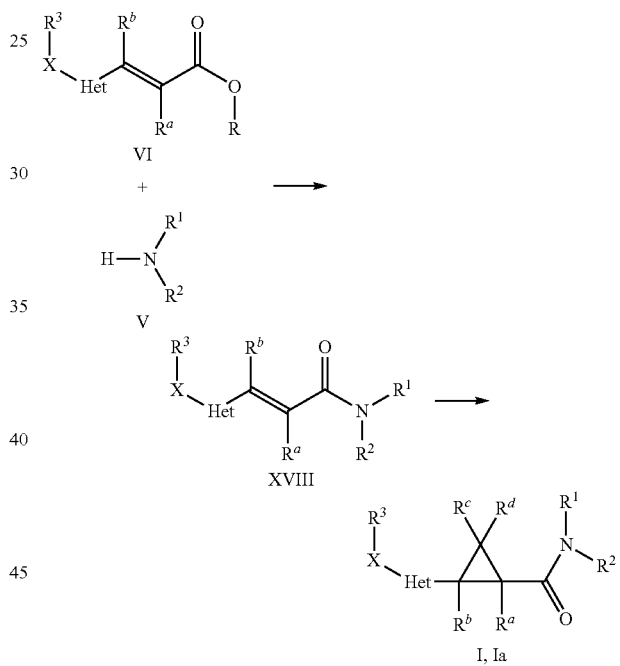

In the compound of the formula XVII the groups Het, $R^a$ and $R^b$ are defined as in the compounds of the formulae I and Ia and, in addition, any functional groups can be present in protected form or in the form of precursor groups which are then converted into the desired final groups. The group R in the compound of the formula XVII is defined as in the compound of the formula IV and can thus be hydrogen, $(C_1-C_4)$-alkyl or benzyl, for example. The group $L^2$ in the compound of the formula XVII is defined as in the compounds of the formulae XI and XV. The explanations given above on the reaction of the compound of the formula VII with the compound of the formula VIII, the reaction of the compound of the formula IX with the compound of the formula X, and the reaction of the compounds of the formulae XI and XV with the compound of the formula XII apply correspondingly to the reaction of the compound of the formula XI with the compound of the formula VIII, the reaction of the compound of the formula XV with the compound of the formula X, and the reaction of the compound of the formula XVII with the compound of the formula XII, respectively. Similarly as explained above, the formation of a compound of the formula XVII in which R is hydrogen may thus include the cleavage of an ester group to provide a carboxylic acid group. Analogously, in a further approach for the synthesis of a compound of the formula VI, the starting compounds of the formulae XIV and VIII, or the starting compounds of the formulae XVI and X, may be reacted to give an intermediate which differs from the compound of the formula XVII in that it contains a group HX— instead of the group $L^2$, wherein X is chosen from O, O—$CH_2$, S, NH and N(($C_1-C_4$)-alkyl) and into which the group $R^3$ is then introduced by reaction with a compound of the formula XIII to give a compound of the formula VI.

Instead of introducing the moiety —$NR^1R^2$ at the final stage of the synthesis of a compound of the formula I or Ia by reacting an intermediate of the formula IV with an amine of the formula V, it is also possible to introduce the said moiety at an earlier stage. For example, in one such synthetic strategy a heteroarylacrylic acid derivative of the formula VI, which can be prepared as outlined above, is reacted with an amine of the formula V to give a heteroarylacrylamide of the formula XVIII which is then subjected to a cyclopropanation reaction to give a compound of the formula I or Ia.

In the compound of the formula XVIII the groups Het, X, $R^a$, $R^b$, $R^1$, $R^2$ and $R^3$ are defined as in the compounds of the formulae I and Ia and, in addition, any functional groups can be present in protected form or in the form of precursor groups which are then converted into the desired final groups. The explanations given above on the amide formation from the compound of the formula IV with the compound of the formula V, and on the cyclopropanation of the compound of the formula VI to give the compound of the formula IV, apply correspondingly to the reaction of the compound of the formula VI with the compound of the formula V, and the cyclopropanation of the compound of the formula XVIII, respectively. Thus, for example, a compound of the formula VI in which the group COOR is an ester group, as well as a compound in which the group COOR is a carboxylic acid group COOH, can be reacted with a compound of the formula V, where in the latter case the carboxylic acid group is preferably activated or converted into a reactive carboxylic acid derivative group, for example into the carboxylic acid chloride. Examples of cyclopropanation reagents, by which the conversion of the compound of the formula XVIII into the compound of the formula I or Ia can be effected, are trimethylsulfonium iodide and trimethylsulfoxonium iodide in the presence of a base such as sodium hydride.

Other such synthetic strategies start from a compound of the formula XVII, which can be prepared as outlined above and which can be converted into a compound of the formula I or Ia via several approaches. In one of them, the compound of the formula XVII is first reacted with an amine of the formula V to give a compound of the formula XIX which compound is subsequently subjected to a cyclopropanation reaction to give a compound of the formula XX which compound is finally reacted with a compound of the formula XII to give a compound of the formula I or Ia. In another one, the compound of the formula XVII is first subjected to a cyclopropanation reaction to give a compound of the formula XXI which compound is subsequently reacted with an amine of the formula V to give a compound of the formula XX which compound is finally reacted with a compound of the formula XII to give a compound of the formula I or Ia.

carboxylic acid or a derivative thereof and an amine, on the cyclopropanation reaction and on the reaction of a compound containing a leaving group $L^2$ with a compound of the formula XII apply correspondingly to the reaction of the compounds of the formulae XVII and XXI with a compound of the formula V, the cyclopropanation of the compounds of the formulae XVII and XIX, and the reaction of the compound of the formula XX with the compound of the formula XII, respectively. Thus, for example, in case the group X is a direct bond, the group $R^3$—X is preferably introduced by means of a compound of the formula XII in which Y is a boronic acid group or a derivative thereof, for example a boronic acid of the formula $R^3$—$B(OH)_2$, under the conditions of the Suzuki reaction, as explained above. In further approaches for the synthesis of a compound of the formula I or Ia, a compound of the formula XIX or a compound of the formula XXI is first reacted with a compound of the formula XII to give the respective compounds which contain the moiety $R^3$—X— instead of the group $L^2$, which compounds are subsequently subjected to a cyclopropanation or a reaction with a compound of the formula V, respectively.

Instead of forming the cyclopropane ring, which is depicted in formulae I and Ia, by introduction of the moiety

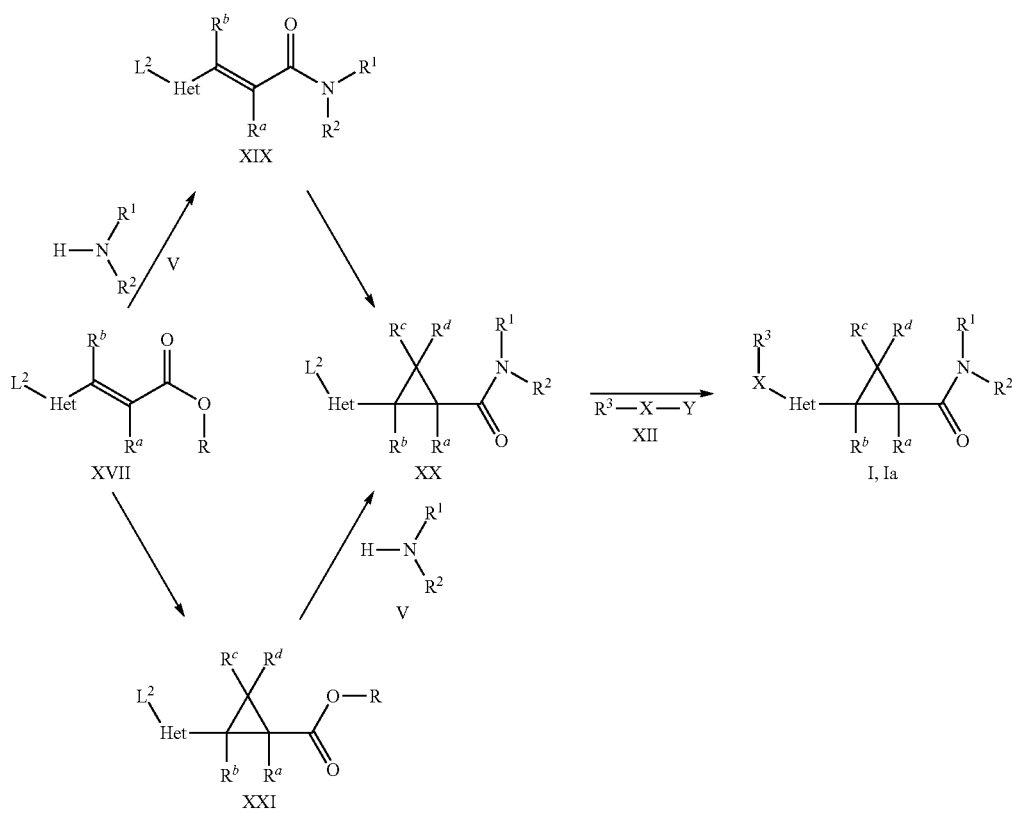

In the compounds of the formulae XIX, XX and XXI the groups Het, $R^a$, $R^b$, $R^c$, $R^d$, $R^1$ and $R^2$ are defined as in the compounds of the formulae I and Ia and, in addition, any functional groups can be present in protected form or in the form of precursor groups which are then converted into the desired final groups. The group $L^2$ in the compounds of the formulae XIX, XX and XXI is defined as in the compounds of the formulae XI and XV. The group R in the compound of the formula XXI is defined as in the compound of the formula IV. The explanations given above on the amide formation from a $CR^cR^d$ in a cyclopropanation of an intermediate which comprises the moiety Het-$CR^b$=$CR^a$—CO, the cyclopropane ring can also be formed by introducing another moiety in a cyclopropanation reaction, for example by the cyclopropanation of an intermediate which comprises the moiety Het-$CR^b$=$CR^cR^d$ such as a compound of the formula XXII or XXIII. As cyclopropanation reagents for the conversion of a compound of the formula XXII or XXIII into a compound of the formula IV or XXI, respectively, diazoalkanoic acid esters such as ethyl diazoacetate, for example, can be used which are preferably employed in the presence of a transition metal catalyst, for example a ruthenium compound or a copper compound, in an inert solvent such a chlorinated hydrocarbon, for example dichloromethane. The obtained compound of the formula XXI can subsequently be converted into a compound of the formula I or Ia as outlined afore, or reacted with a compound of the formula XII to give a compound of the formula IV as explained above with respect to replacement of the group $L^2$ with the group $R^3$—X— in other intermediates.

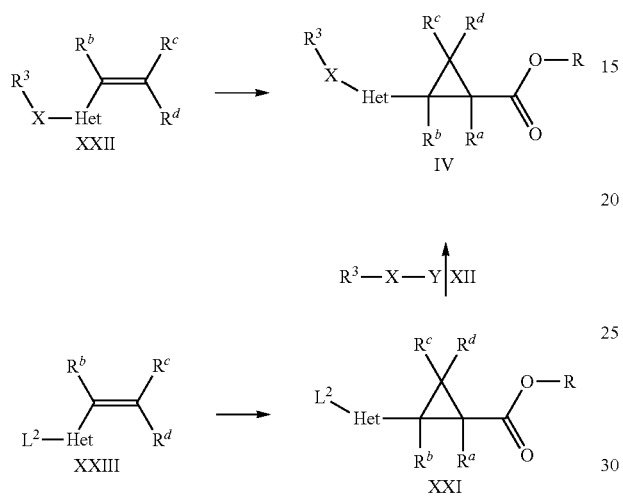

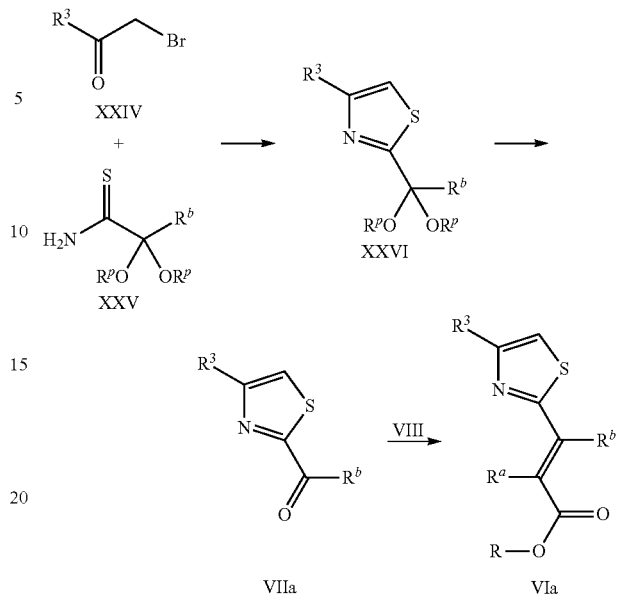

In the compounds of the formulae XXII and XXIII the groups Het, X, $R^b$, $R^c$, $R^d$ and $R^3$ are defined as in the compounds of the formulae I and Ia and, in addition, any functional groups can be present in protected form or in the form of precursor groups which are then converted into the desired final groups. The group $L^2$ in the compound of the formulae XXIII is defined as in the compounds of the formulae XI and XV. The compounds of the formulae XXII and XXIII can be obtained from the aldehydes or ketones of the formulae VII and XI, respectively, in a Wittig reaction, for example.

Further synthetic strategies for the preparation of compounds of the invention include the assembly of the group Het in a ring-forming reaction from starting compounds which may contain the groups $R^3$—X— or part of this group or a protected form or precursor thereof which is then modified in subsequent reaction steps. For example, compounds of the formulae I and Ia in which the group Het is a thiazole ring and the group X is a direct bond, can be prepared by reacting a 2-bromo-1-$R^3$-ethanone of the formula XXIV, in which the $CH_2$ group can optionally be substituted by a suitable substituent representing $R^5$, for example an alkyl substituent, with a 2-oxo-thiocarboxamide in which the oxo group is protected, for example as a ketal or acetal, for example with a 2,2-diethoxythioacetamide derivative of the formula XXV, to give a compound of the formula XXVI. Subsequent deprotection of the oxo group yields a compound of the formula VIIa which is then reacted with a compound of the formula VIII, for example in a Wittig reaction or a Wittig-Horner reaction, to give an intermediate of the formula VIa, whose reaction with an amine of the formula V and cyclopropanation with a cyclopropanation reagent introducing the moiety $CR^cR^d$ finally provides a compound of the formula I or Ia as outlined above.

In the compounds of the formulae XXIV, XXV, XXVI, VIa and VIIa the groups $R^a$, $R^b$ and $R^3$ are defined as in the compounds of the formulae I and Ia and, in addition, any functional groups can be present in protected form or in the form of precursor groups which are then converted into the desired final groups. Like the $CH_2$ group in the compound of the formula XXIV, the thiazole ring in the compounds of the formulae XXVI, VIa and VIIa can be substituted by a suitable substituent such as an alkyl group. The group R in the compound of the formula VIa is defined as in the compound of the formula VI and can thus be hydrogen, $(C_1-C_4)$-alkyl or benzyl, for example, where the formation of a compound of the formula VIa in which R is hydrogen may include the cleavage of an initially formed ester. The groups $R^p$ in the compounds of the formulae XXV and XXVI can be alkyl groups, such as methyl or ethyl, or together be an alkanediyl group, such as an 1,2-ethanediyl group. The reaction of the compounds of the formulae XXIV and XXV is generally carried out in a solvent, for example an alcohol like as methanol or ethanol, an ester like ethyl acetate or butyl acetate, or an ether like THF, dioxane or DME, at temperatures from about 20° C. to about 80° C. The cleavage of the acetal or ketal group in the compound of the formula XXVI to give the free oxo group can be performed by treatment with a dilute acid, for example hydrochloric acid or sulfuric acid, at temperatures from about 20° C. to about 60° C., and the subsequent reaction with the compound of the formula VIII under the condition outlined above with respect to the reaction of the compounds of the formulae VII and VIII.

As another example of a process for the preparation of compounds of the invention which includes the assembly of the group Het in a ring-forming reaction, the preparation of compounds in which the group Het is a pyrimidine ring, the group X is a direct bond and the group $R^b$ is hydrogen, may be mentioned. Such compounds can be obtained by reacting an amidine of the formula XXVII with a suitable triformylmethane derivative, for example a 2-dimethylaminomethylene-1,3-bis(dimethylimmonio)propane salt like the bis(tetrafluoroborate) of the formula XXVIII which is described in M. Keshavarz-K. et al., Synthesis (1988) 641, with subsequent hydrolysis of the dimethylimmonio group to give the compound of the formula VIIb which is then reacted with a compound of the formula VII, for example in a Knoevenagel reaction, to give an intermediate of the formula VIb whose reaction with an amine of the formula V and cyclopropanation with a cyclopropanation reagent introducing the moiety $CR^cR^d$ finally provides a compound of the formula I or Ia as outlined above.

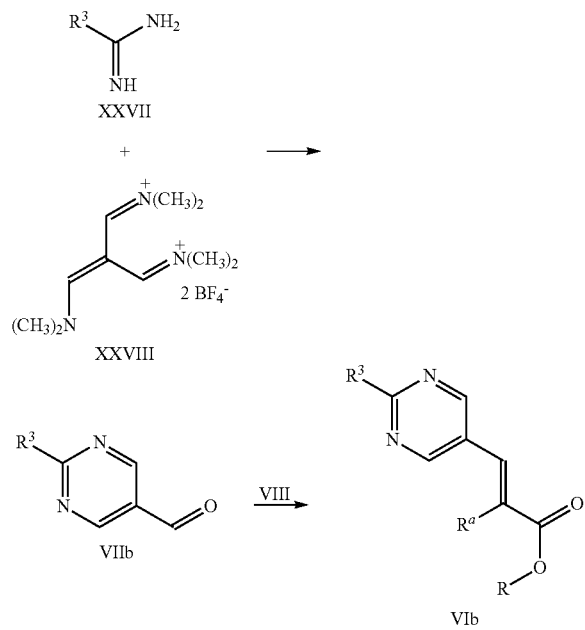

In the compounds of the formulae XXVII, XXVIII, VIb and VIIb the groups $R^a$ and $R^3$ are defined as in the compounds of the formulae I and Ia and, in addition, any functional groups can be present in protected form or in the form of precursor groups which are then converted into the desired final groups. The group R in the compound of the formula VIb is defined as in the compound of the formula VI and can thus be hydrogen, $(C_1-C_4)$-alkyl or benzyl, for example, where the formation of a compound of the formula VIb in which R is hydrogen may include an ester cleavage. As applies to starting materials in processes for the preparation of compounds of the formulae I and Ia in general, the compounds of the formula XXVII may also be employed in the form of salts, for example acid addition salts with hydrochloric acid. The reaction of the compound of the formula XXVII or its salt with the compound of the formula XXVIII is generally carried out in a solvent, for example an alcohol like methanol or ethanol, an ether like THF, dioxane or DME, or an amide like DMF or NMP, in the presence of a base, for example an alkali metal alkoxide like sodium methoxide, sodium ethoxide or potassium tert-butoxide, at temperatures from about 20° C. to about 100° C. After treatment of the reaction mixture with water, the obtained aldehyde of the formula VIIb is then reacted with a compound of the formula VIII under the condition outlined above with respect to the reaction of the compounds of the formulae VII and VIII.

Instead of assembling the group Het from starting compounds in a ring forming reaction to give an intermediate which is later subjected to a cyclopropanation reaction, the synthesis of a compound of the invention may also start from a suitably substituted cyclopropane derivative a substituent of which is converted into the group Het. For example, in cyclopropane-1,2-dicarboxylic acid, or a derivative thereof, one of the two carboxylic acid groups can be converted into a heteroaryl group and the second carboxylic acid group into the group $CO-NR^1R^2$. For example, one of the carboxylic acid groups can first be transformed into a functional group such as a thioamide, a hydrazide, an amidoxime, a nitrile or another group, and this group then cyclized by well-known processes for the assembly of heteroaromatic rings to give a heteroaromatic ring such as a thiazole, an oxadiazole, a tetrazole or another ring.

Further compounds of the formulae I and Ia can be obtained from suitable intermediates or compounds of the formulae I and Ia prepared according to the above-described processes by functionalization or modification of contained functional groups according standard procedures, for example by esterification, amidation, hydrolysis, etherification, alkylation, acylation, sulfonylation, oxidation, reduction, conversion into salts, and others. As specific examples of oxidation reactions, the oxidation of ring nitrogen atoms to give N-oxides and the oxidation of sulfur atoms to give sulfoxides or sulfones may be mentioned, which are preferably carried out with hydrogen peroxide or a peracid such as 3-chloroperbenzoic acid.

All reactions used in the above-described syntheses of the compounds of the formulae I and Ia are per se well-known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. As already indicated above, depending on the circumstances of the individual case, in order to avoid an unwanted course of a reaction or side reactions during the synthesis of a compound, it can generally be necessary or advantageous to temporarily block functional groups by introducing protective groups and deprotect them at a later stage of the synthesis, or introduce functional groups in the form of precursor groups which later are converted into the desired functional groups. As examples of protecting groups, amino protecting groups such as the tert-butyloxycarbonyl group (Boc) which can be removed by treatment with trifluoroacetic acid (TFA), the benzyloxycarbonyl group which can be removed by catalytic hydrogenation, or the fluoren-9-ylmethoxycarbonyl group which can be removed by treatment with piperidine, carboxylic acid protecting groups such as the tert-butyl ester group which can be deprotected by treatment with TFA, or the benzyl ester group which can be deprotected by catalytic hydrogenation, or aldehyde and ketone protecting groups such as the dimethyl or diethyl acetal group and ketal group or the ethylene acetal group and ketal group which can be deprotected with dilute acid, may be mentioned. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person. If desired, the obtained compounds of formulae I and Ia, as well as any intermediate compounds, can be purified by customary purification procedures, for example by recrystallization or chromatography.

The compounds of the formulae I and Ia are useful pharmacologically active, or pharmaceutically active compounds, which modulate the expression of endothelial NO synthase, and more specifically upregulate, or stimulate, the expression, or transcription, of endothelial NO synthase, and which can be employed as pharmaceuticals, or active ingredients of medicaments, for the treatment of various diseases. In the context of the present invention, treatment is understood as comprising both therapy, including alleviation and cure, of diseases and disease symptoms and prevention and prophylaxis of diseases and disease symptoms, such as, for example, the prevention of the appearance of asthmatic disease symptoms or the prevention of myocardial infarction or of myocardial reinfarction in affected patients. The diseases or disease symptoms can be acute or chronic. Diseases which can be treated with the compounds of the formulae I and Ia include, for example, cardiovascular diseases like stable and unstable angina pectoris, coronary heart disease, coronary artery disease, Prinzmetal angina (spasm), acute coronary syndrome, cardiac insufficiency, heart failure, myocardial infarction, stroke, thrombosis, peripheral artery occlusive disease (=PAOD), endothelial dysfunction, atherosclerosis, restenosis, endothel damage after PTCA (=percutaneous transluminal coronary angioplasty), hypertension including essential hypertension, pulmonary hypertension and secondary hypertension (renovascular hypertension, chronic glomerulonephritis), erectile dysfunction, and ventricular arrhythmia. Further, the compounds of the formulae I and Ia can be used to lower the cardiovascular risk of postmenopausal women or after intake of contraceptives. Compounds of the formulae I and Ia can additionally be used in the treatment, including therapy and prevention, of diabetes and diabetes complications such as nephropathy or retinopathy, angiogenesis, asthma bronchiale, chronic renal failure, cirrhosis of the liver, osteoporosis, restricted memory performance or a restricted ability to learn. Preferred indications are stable angina pectoris, coronary heart disease, cardiac insufficiency, hypertension, endothelial dysfunction, atherosclerosis and diabetes complications.

The compounds of the formulae I and Ia can be used in combination with other pharmacologically active compounds or pharmaceuticals, preferably with compounds which are able to enhance the effect of the compounds according to the formulae I and Ia. Examples of such other compounds include statins; ACE inhibitors; AT1 antagonists; argininase inhibitors; PDE V inhibitors; calcium antagonists; alpha blockers; beta blockers; metimazol and analogous compounds; arginine; tetrahydrobiopterin; vitamins, in particular vitamin C and vitamin B6; niacine.

The compounds of the formulae I and Ia and their physiologically acceptable salts, optionally in combination with other pharmacologically active compounds, can be administered to animals, preferably to mammals, and in particular to humans, as pharmaceuticals by themselves, in mixtures with one another, or in the form of pharmaceutical compositions. Further subjects of the present invention therefore also are the compounds of the formulae I and Ia and their physiologically acceptable salts for use as pharmaceuticals, their use as modulating agents, and more specifically as stimulating agents or upregulating agents, of the expression or transcription of endothelial NO synthase, for example in conditions in which an increased expression of said enzyme or an increased NO level or the normalization of a decreased NO level in a patient is desired, and in particular their use in the treatment, including therapy and prevention, of the above-mentioned diseases or syndromes, as well as their use for the preparation or manufacture of medicaments for these purposes. Furthermore, a subject of the present invention are pharmaceutical compositions, or pharmaceutical preparations, which comprise at least one compound of the formulae I or Ia and/or a physiologically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, for example in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I or Ia and/or its physiologically acceptable salts present in the pharmaceutical compositions is chosen such that it is effective for the desired purpose, and normally ranges from about 0.2 to about 800 mg, preferably from about 0.5 to about 500 mg, in particular from about 1 to about 200 mg, per dose, but depending on the type of the pharmaceutical composition it may also be higher. The pharmaceutical compositions usually comprise from about 0.5 to about 90 percent by weight of the compounds of the formulae I or Ia and/or their physiologically acceptable salts. The production of the pharmaceutical compositions can be carried out in a manner known per se. To this end, one or more compounds of the formulae I or Ia and/or their physiologically acceptable salts together with one or more solid or liquid pharmaceutical carrier substances (or vehicles) and/or additives (or auxiliary substances) and, if a combination medicament is desired, other pharmacologically active compounds having therapeutic or prophylactic action are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formulae I and Ia and their physiologically acceptable salts and to use the resulting lyophilisates, for example, for preparing compositions for injection or infusion. Suitable carriers for microcapsules, implants or rods are, for example, copolymers of glycolic acid and lactic acid. Besides the compound or compounds according to the invention and carrier substances, the pharmaceutical compositions can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I or Ia to be administered and/or of a physiologically acceptable salt thereof depends on the individual case and, as is customary, has to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compound used, on whether the use is for the therapy of a acute or chronic disease or prophylactic, or on whether other active compounds are administered in addition to compound of the formula I or Ia. In general, a daily dose from about 0.01 mg/kg to about 100 mg/kg, preferably from about 0.1 mg/kg to about 10 mg/kg, in particular from about 0.3 mg/kg to about 5 mg/kg (in each case mg per kg of bodyweight) is appropriate for administration to an adult weighing about 75 kg in order to obtain the desired results. The daily dose can be administered in a single dose or, in particular when larger amounts are administered, divided into several, for example two, three or four individual doses. In some cases, depending on the individual response, it may be necessary to deviate upwards or downwards from the given daily dose.

The compounds of the formulae I and Ia can also be used for other purposes than those indicated in the foregoing. Non-limiting examples include the use as diagnostics, for example the use in methods for determining the activity of endothelial NO synthase in biological samples, the use as biochemical tools and the use as intermediates for the preparation of further compounds, for example further pharmacologically active compounds.

EXAMPLES

Compounds containing a basic group which were purified by preparative high pressure liquid chromatography (HPLC), specifically on reversed phase (RP) material, using an eluent which contained trifluoroacetic acid, were in part obtained in the form of acid addition salts with trifluoroacetic acid (TFA) which is not depicted in the formulae in the examples. The compounds were characterized by analytical HPLC and/or mass spectrometry (MS) and/or nuclear magnetic resonance spectrometry (NMR).

Example 1 trans-2-[6-(4-Fluoro-phenyl)-pyridin-3-yl]-cyclopropanecarboxylic acid (2,3-difluoro-phenyl)-amide trifluoroacetic acid salt

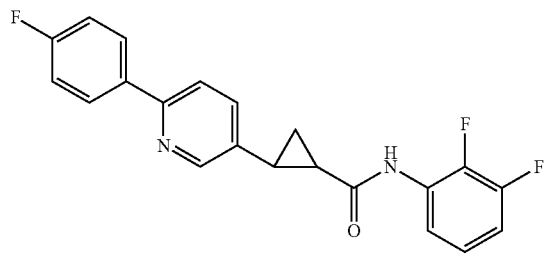

(a) 5-Bromo-2-(4-fluoro-phenyl)-pyridine 22.4 g (160 mmol) of 4-fluoro-benzeneboronic acid, 34 g (153.5 mmol) of 2,5-dibromopyridine and 1.24 g of tetrakis(triphenylphosphine)palladium were dissolved in 240 ml of ethanol and 480 ml of toluene. 480 ml of a 2 N sodium carbonate solution were added and the resulting mixture was heated to 50° C. with stirring for 2 h. After addition of 400 ml of ethyl acetate the mixture was filtered, the phases were separated and the organic phase was washed with a saturated sodium chloride solution, dried and evaporated. The obtained product was purified by column chromatography (silica gel, dichloromethane/heptane 1:1) and preparative HPLC (RP 18). Yield: 12 g.

MS: m/e=253 (M+H)+

(b) 3-[6-(4-Fluoro-phenyl)-pyridin-3-yl]-acrylic acid ethyl ester 9.30 g (36.9 mmol) of 5-bromo-2-(4-fluoro-phenyl)-pyridine were mixed with 100 ml of triethylamine, 2.06 g (9.2 mmol) of palladium acetate, 2.80 g (9.2 mmol) of tri)orthotolyl)phosphine and 6.47 g (64.6 mmol) of acrylic acid ethyl ester and heated to 90° C. for 2 h. The reaction mixture was evaporated, taken up in water and extracted with ethyl acetate. The combined organic phases were dried and evaporated, and the residue was subjected to column chromatography (silica gel, n-heptane/ethyl acetate 3:1). Yield: 7.7 g.

MS: m/e=272 (M+H)+

(c) trans-2-[6-(4-Fluoro-phenyl)-pyridin-3-yl]-cyclopropanecarboxylic acid ethyl ester 100 ml of dry dimethyl sulfoxide were added slowly to a mixture of 9.30 g (42.3 mmol) of trimethylsulfoxonium iodide and 976 mg (40.1 mmol) of sodium hydride. The mixture was stirred at room temperature for 15 min, and then 8.5 g (31.3 mmol) of 3-[6-(4-fluoro-phenyl)-pyridin-3-yl]-acrylic acid ethyl ester were added. The reaction mixture was stirred at room temperature for 18 h and then poured onto ice/water and extracted with ethyl acetate. The combined organic phases were dried and evaporated. The obtained raw product was purified by column chromatography (silica gel, dichloromethane). Yield: 6.75 g.

MS: m/e=286 (M+H)+

(d) trans-2-[6-(4-Fluoro-phenyl)-pyridin-3-yl]-cyclopropanecarboxylic acid 3.00 g (10.5 mmol) of trans-2-[6-(4-fluoro-phenyl)-pyridin-3-yl]-cyclopropanecarboxylic acid ethyl ester and 378 mg (15.8 mmol) of lithium hydroxide were dissolved in a mixture of 27 ml of methanol, 5 ml of dioxane and 3 ml of water, and the mixture was heated at 70° C. for 2 h. Subsequently, the mixture was evaporated to dryness, the residue was taken up in water and the pH was adjusted to 4 with acetic acid. The precipitate was isolated by filtration and purified by column chromatography (silica gel, dichloromethane/methanol, gradient from 98:2 to 95:5). Yield: 2.2 g.

(e) trans-2-[6-(4-Fluoro-phenyl)-pyridin-3-yl]-cyclopropanecarboxylic acid chloride hydrochloride 200 mg (0.78 mmol) of trans-2-[6-(4-fluoro-phenyl)-pyridin-3-yl]-cyclopropanecarboxylic acid were dissolved in 5 ml of thionyl chloride and heated under reflux for 3 h. The mixture was evaporated to dryness. The residual oil was used in the next step without further purification.

(f) trans-2-[6-(4-Fluoro-phenyl)-pyridin-3-yl]-cyclopropanecarboxylic acid (2,3-difluoro-phenyl)-amide trifluoroacetic acid salt A solution of 121 mg (0.94 mmol) of 2,3-difluoroaniline and 158 mg (1.56 mmol) of triethylamine in 2 ml of dichloromethane was added to the raw trans-2-[6-(4-fluoro-phenyl)-pyridin-3-yl]-cyclopropanecarboxylic acid chloride hydrochloride prepared in step (e). The reaction mixture was stirred at room temperature for 10 min, then poured onto ice and extracted with ethyl acetate. The combined organic phases were dried and evaporated. The obtained raw product purified by preparative HPLC (RP 18, acetonitrile/water, +0.01% TFA). Yield: 280 mg.

MS: m/e=369 (M+H)$^+$

The compounds of examples 2 to 10 were prepared as described in Example 1(f) by replacing 2,3-difluoroaniline with the respective amine.

Example 2 trans-2-[6-(4-Fluoro-phenyl)-pyridin-3-yl]-cyclopropanecarboxylic acid thiazol-2-ylamide trifluoroacetic acid salt

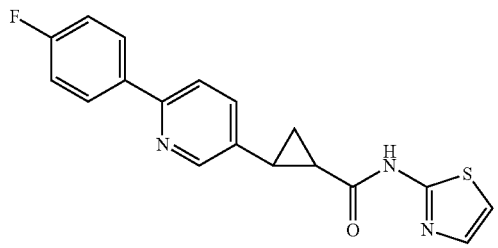

MS: m/e=340 (M+H)$^+$

Example 3 trans-2-[6-(4-Fluoro-phenyl)-pyridin-3-yl]-cyclopropanecarboxylic acid prop-2-ynylamide

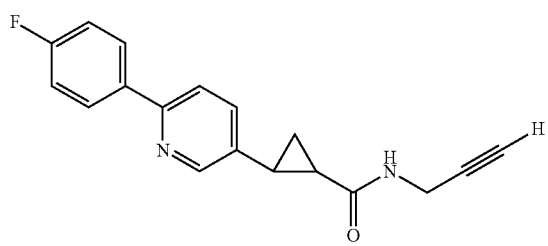

MS: m/e=295 (M+H)$^+$

Example 4 trans-2-[6-(4-Fluoro-phenyl)-pyridin-3-yl]-cyclopropanecarboxylic acid (1H-[1,2,4]triazol-3-yl)-amide

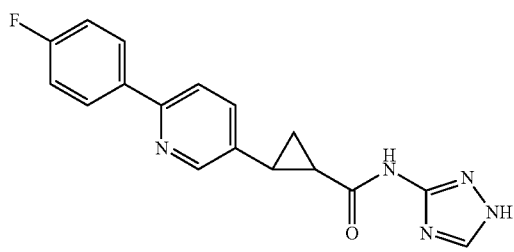

MS: m/e=324 (M+H)$^+$

Example 5 trans-2-[6-(4-Fluoro-phenyl)-pyridin-3-yl]-cyclopropanecarboxylic acid pyridin-2-ylamide trifluoroacetic acid salt

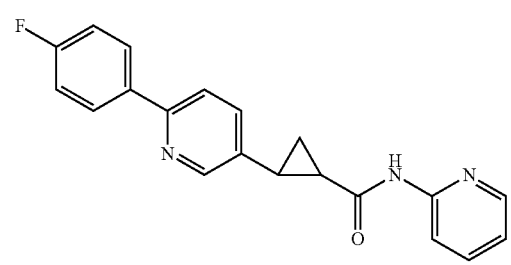

MS: m/e=334 (M+H)$^+$

Example 6 trans-2-[6-(4-Fluoro-phenyl)-pyridin-3-yl]-cyclopropanecarboxylic acid quinolin-8-ylamide trifluoroacetic acid salt

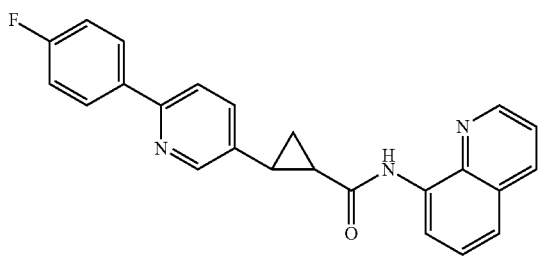

MS: m/e=384 (M+H)$^+$

Example 7

2-({trans-2-[6-(4-Fluoro-phenyl)-pyridin-3-yl]-cyclopropanecarbonyl}-amino)-benzamide trifluoroacetic acid salt

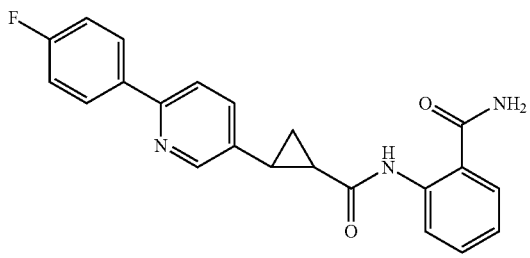

MS: m/e=376 (M+H)⁺

Example 8

{trans-2-[6-(4-Fluoro-phenyl)-pyridin-3-yl]-cyclopropyl}-((R)-2-methoxymethyl-pyrrolidin-1-yl)-methanone trifluoroacetic acid salt

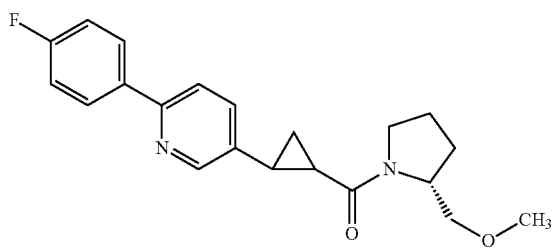

MS: m/e=355 (M+H)⁺

Example 9 trans-2-[6-(4-Fluoro-phenyl)-pyridin-3-yl]-cyclopropanecarboxylic acid tert-butylamide trifluoroacetic acid salt

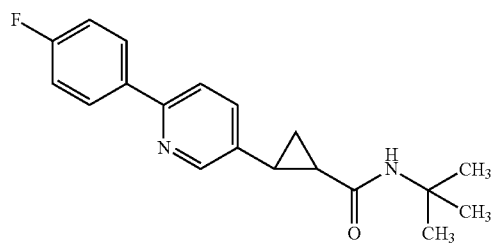

MS: m/e=313 (M+H)⁺

Example 10 trans-2-[6-(4-Fluoro-phenyl)-pyridin-3-yl]-cyclopropanecarboxylic acid (2-acetylamino-phenyl)-amide trifluoroacetic acid salt

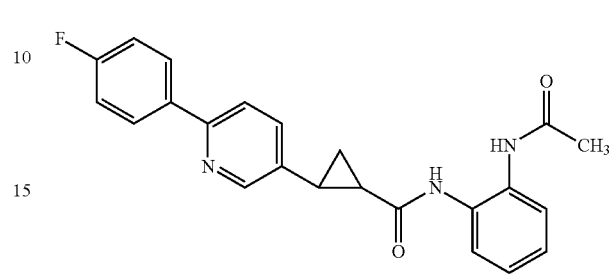

MS: m/e=390 (M+H)⁺

Example 11

General Procedure 1: Preparation of trans-2-[6-(4-fluoro-phenyl)-pyridin-3-yl]-cyclopropanecarboxamides of the Formula Ib

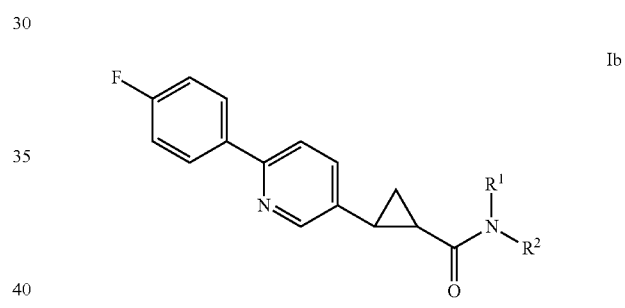

0.192 mmol of the respective amine were dissolved in 1 ml of dichloromethane and 48.6 mg (0.48 mmol) of triethylamine and 56.0 mg (0.18 mmol) of trans-2-[6-(4-fluoro-phenyl)-pyridin-3-yl]-cyclopropanecarboxylic acid chloride hydrochloride (Example 1(e)), dissolved in 1 ml of dichloromethane, were added. The reaction mixture was stirred at room temperature overnight, filtered, washed with 20 ml of a 5% sodium hydrogencarbonate solution and 20 ml of a 5% sodium chloride solution, dried over Chromabond® XTR and evaporated. The obtained raw product was purified by preparative HPLC (RP 18, acetonitrile/water, +0.01% TFA).

According to general procedure 1, the example compounds listed in Table 1 were prepared which were obtained in the form of their trifluoroacetic acid salts. The compounds may be named as N-substituted trans-2-[6-(4-fluoro-phenyl)-pyridin-3-yl]-cyclopropanecarboxamide trifluoroacetic acid salt, for example as trans-2-[6-(4-fluoro-phenyl)-pyridin-3-yl]-cyclopropanecarboxylic acid ethyl-(2-fluoro-phenyl)-amide trifluoroacetic acid salt or N-ethyl-N-(2-fluoro-phenyl)-trans-2-[6-(4-fluoro-phenyl)-pyridin-3-yl]-cyclopropanecarboxamide trifluoroacetic acid salt in the case of Example 12, or as {trans-2-[6-(4-fluoro-phenyl)-pyridin-3-yl]-cyclopropyl}-heterocyclyl-methanone trifluoroacetic acid salt, for example as {trans-2-[6-(4-fluoro-phenyl)-pyridin-3-yl]-cyclopropyl}-(pyrrolidin-1-yl)-methanone trifluo- TABLE 1
Example compounds of the formula Ib
| Example No. | R¹ N R² | MS: m/e = |
|---|---|---|
| 12 | 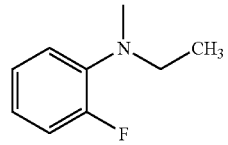 | 379 (M + H)⁺ |
| 13 | 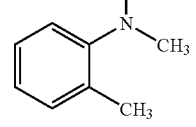 | 361 (M + H)⁺ |
| 14 | 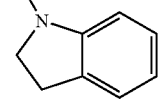 | 359 (M + H)⁺ |
| 15 | 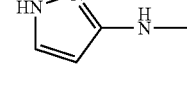 | 323 (M + H)⁺ |
| 16 | 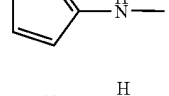 | 324 (M + H)⁺ |
| 17 | 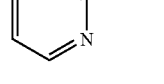 | 335 (M + H)⁺ |
| 18 | 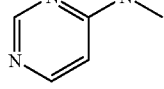 | 335 (M + H)⁺ |
| 19 | 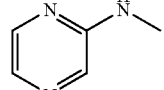 | 335 (M + H)⁺ |
| 20 | 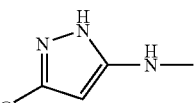 | 337 (M + H)⁺ |
| 21 | 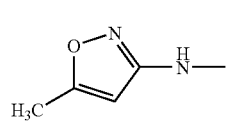 | 338 (M + H)⁺ |
TABLE 1-continued
Example compounds of the formula Ib
| Example No. | R¹ N R² | MS: m/e = |
|---|---|---|
| 22 |  | 375 (M + H)⁺ |
| 23 | 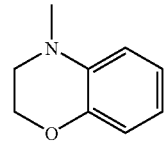 | 348 (M + H)⁺ |
| 24 | 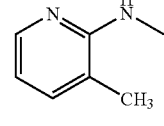 | 348 (M + H)⁺ |
| 25 | 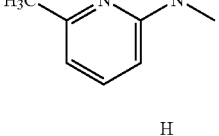 | 352 (M + H)⁺ |
| 26 | 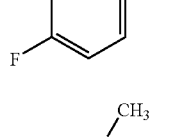 | 351 (M + H)⁺ |
| 27 | 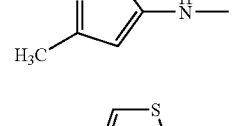 | 396 (M + H)⁺ |
| 28 | 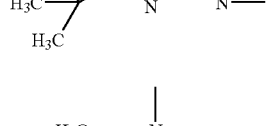 | 313 (M + H)⁺ |
| 29 | 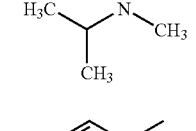 | 324 (M + H)⁺ |
| 30 | 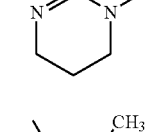 | 324 (M + H)⁺ |
| 31 | 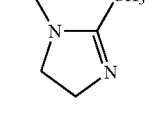 | 325 (M + H)⁺ |
roacetic acid salt in the case of Example 46, or in another manner, depending on the structure of the individual compound.

TABLE 1-continued

Example compounds of the formula Ib

| Example No. | R¹\N\R² | MS: m/e = |
|---|---|---|
| 32 | H₃C-CH(CH₃)-CH₂-N(CH₃)- | 327 (M + H)⁺ |
| 33 | H₃C-CH(CH₃)-N(CH₃)-CH₂CH₃ | 327 (M + H)⁺ |
| 34 | N-methyl-2-(CF₃)-pyrrolidinyl | 379 (M + H)⁺ |
| 35 | (H₃C)₂CH-N(CH₃)₂ | 327 (M + H)⁺ |
| 36 | 1-methyl-4,4-dimethyl-imidazoline | 338 (M + H)⁺ |
| 37 | 3-fluoro-1-methyl-piperidinyl | 343 (M + H)⁺ |
| 38 | 2,6-dimethyl-1-methyl-piperidinyl | 353 (M + H)⁺ |
| 39 | 2,6-dimethyl-4-methyl-piperazinyl | 354 (M + H)⁺ |
| 40 | 4,4-difluoro-1-methyl-piperidinyl | 361 (M + H)⁺ |
| 41 | N-methyl-norbornyl-amine | 337 (M + H)⁺ |
| 42 | 3-(methylsulfonyl)-1-methyl-pyrrolidinyl | 389 (M + H)⁺ |
| 43 | 2-(methoxymethyl)-1-methyl-pyrrolidinyl | 355 (M + H)⁺ |
| 44 | (2-fluorophenyl)-NH- | 351 (M + H)⁺ |
| 45 | phenyl-NH- | 333 (M + H)⁺ |
| 46 | 1-methyl-pyrrolidinyl | 311 (M + H)⁺ |
| 47 | cyclopropyl-NH- | 297 (M + H)⁺ |
| 48 | 1-azetidinyl | 297 (M + H)⁺ |

Example 49 trans-2-[6-(2-Fluoro-phenyl)-pyridin-3-yl]-cyclopropanecarboxylic acid dimethylamide trifluoroacetic acid salt

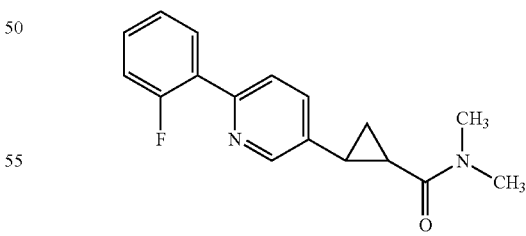

5 ml of dimethyl sulfoxide were added slowly to a mixture of 0.928 g (4.22 mmol) of trimethylsulfoxonium iodide and 96 mg (4.03 mmol) of sodium hydride. The mixture was stirred at room temperature for 15 min, and then 850 mg (3.15 mmol) of 3-[6-(2-fluoro-phenyl)-pyridin-3-yl]-N,N-dimethyl-acrylamide were added. The reaction mixture was stirred at room temperature for 18 h, filtered, and the product was purified by preparative RP HPLC eluting with a gradient

Example 50

{trans-2-[4-(2-Fluoro-phenyl)-thiophen-2-yl]-cyclopropyl}-(piperidin-1-yl)-methanone

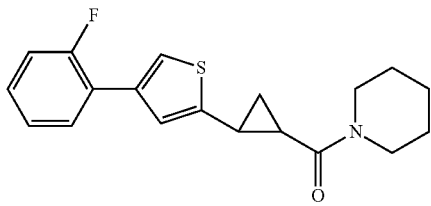

5 ml of dimethyl sulfoxide were added slowly to a mixture of 0.907 g (4.12 mmol) of trimethylsulfoxonium iodide and 98.9 mg (4.12 mmol) of sodium hydride. The mixture was stirred at room temperature for 15 min, 500 mg (1.59 mmol) of 3-[4-(2-fluoro-phenyl)-thiophen-2-yl]-1-(piperidin-1-yl)-propenone were added, and the reaction mixture was stirred at room temperature for 18 h. Then a freshly prepared solution of a further 1 equivalent of trimethylsulfoxonium iodide/sodium hydride in dimethyl sulfoxide was added. The reaction mixture was stirred at room temperature for 16 h, filtered, and the product was purified by preparative RP HPLC eluting with a gradient of 0 to 100% acetonitrile in water (+0.01% TFA). After lyophilization, the product was obtained as a solid. Yield: 155 mg.

MS: m/e=330 (M+H)$^+$

Example 51

[trans-2-(6-Phenoxy-pyridin-3-yl)-cyclopropyl]-(piperidin-1-yl)-methanone

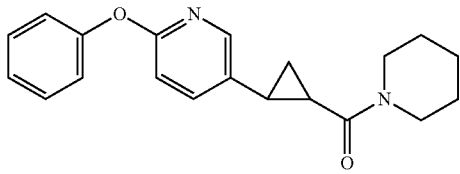

465 mg (2.1 mmol) of trimethylsulfoxonium iodide and 51 mg (2.1 mmol) of sodium hydride were mixed under argon, 5 ml of dimethyl sulfoxide were added, and the mixture was stirred at room temperature for 15 min. 500 mg (1.63 mmol) of 3-(6-phenoxy-pyridin-3-yl)-1-(piperidin-1-yl)-propenone were added, and the reaction mixture was stirred at room temperature for 18 h. Then a freshly prepared solution of further 0.65 equivalents of trimethylsulfoxonium iodide/sodium hydride in dimethyl sulfoxide was added. The reaction mixture was stirred at room temperature for 16 h, 0.1 ml of water were added, the mixture was filtered, and the product was purified by preparative RP HPLC eluting with a gradient of 0 to 100% acetonitrile in water (+0.01% TFA). After lyophilization the product was obtained as a solid. Yield: 162 mg.

MS: m/e=323 (M+H)$^+$

Example 52

{trans-2-[6-(2-Chloro-phenoxy)-pyridin-3-yl]-cyclopropyl}-(piperidin-1-yl)-methanone

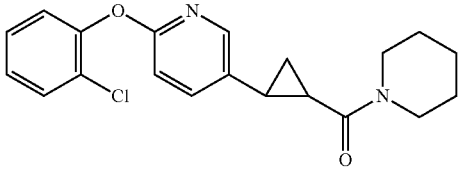

25.8 (0.12 mmol) of trimethylsulfoxonium iodide and 4.8 mg (0.2 mmol) of sodium hydride were mixed under argon, 2 ml of dimethyl sulfoxide were added and the mixture was stirred at room temperature for 15 min. 40 mg (0.09 mmol) of 3-[6-(2-chloro-phenoxy)-pyridin-chloro-phenoxy)-pyridin-3-yl]-1-(piperidin-1-yl)-propenone were added and the reaction solution was stirred at room temperature for 18 h. Then a freshly prepared solution of further 2 equivalents of trimethylsulfoxonium iodide/sodium hydride in dimethyl sulfoxide was added. The reaction mixture was stirred at 60° C. for 5 h, poured onto ice/water, and extracted with ethyl acetate. The combined extracts were dried and evaporated, and the product purified by chromatography. Yield: 8 mg.

MS: m/e=357 (M+H)$^+$

Example 53

3-Phenyl-5-[cis-2-(piperidine-1-carbonyl)-cyclopropyl]-3H-[1,3,4]oxadiazol-2-one

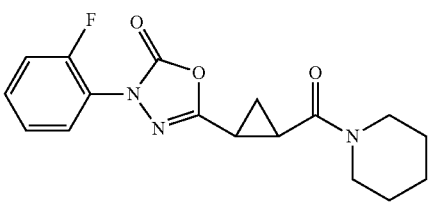

(a) cis-2-(N'-Phenyl-hydrazinocarbonyl)-cyclopropanecarboxylic acid 1.2 g (11.1 mmol) of phenylhydrazine was dissolved in 20 ml of dichloromethane and 1.24 g (11.1 mmol) of 3-oxabicyclo[3.1.0]hexane-2,4-dione were added. The resulting solution was stirred at room temperature for 16 h. The precipitated product was isolated by filtration and washed with dichloromethane. Yield: 1.85 g.

MS: m/e=221 (M+H)$^+$ (b) cis-2-(5-Oxo-4-phenyl-4,5-dihydro-[1,3,4]oxadiazol-2-yl)-cyclopropanecarboxylic acid 1.85 g (8.4 mmol) of cis-2-(N'-phenyl-hydrazinocarbonyl)-cyclopropanecarboxylic acid were dissolved in 20 ml of tetrahydrofuran and 0.823 g (2.8 mmol) of triphosgene were added. The reaction mixture was stirred at room temperature for 16 h. The solvent was removed under reduced pressure, and the residue dissolved in acetonitrile/DMF. The product was purified by preparative RP HPLC eluting with a gradient of 0 to 100% acetonitrile in water (+0.01% TFA). After lyophilization, the product was obtained as a white solid. Yield: 980 mg.

MS: m/e=247 (M+H)$^+$ (c) 3-Phenyl-5-[cis-2-(piperidine-1-carbonyl)-cyclopropyl]-3H-[1,3,4]oxadiazol-2-one 50 mg (0.2 mmol) of cis-2-(5-oxo-4-phenyl-4,5-dihydro-[1,3,4]oxadiazol-2-yl)-cyclopropanecarboxylic acid, 233 mg (2.0 mmol) of NEM and 67 mg (0.2 mmol) of TOTU were dissolved in 2 ml of DMF and stirred at room temperature for 15 min. 17.3 mg (0.2 mmol) of piperidine were added to the reaction solution. After stirring at room temperature for 16 h, the reaction mixture was filtered and the product was purified by preparative RP HPLC eluting with a gradient of 0 to 100% acetonitrile in water (+0.01% TFA). After lyophilization the product was obtained as a white solid. Yield: 44 mg.

MS: m/e=314 (M+H)$^+$

Example 54

(1R,2R)-2-[6-(4-Fluoro-phenyl)-pyridin-3-yl]-cyclopropanecarboxylic acid ethyl ester and (1S,2S)-2-[6-(4-fluoro-phenyl)-pyridin-3-yl]-cyclopropanecarboxylic acid ethyl ester

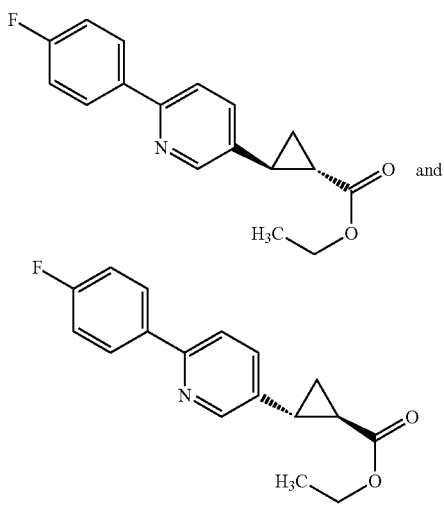

Separation of the racemic mixture of the enantiomers of trans-2-[6-(4-fluoro-phenyl)-pyridin-3-yl]-cyclopropanecarboxylic acid ethyl ester (Example 1(c)) by HPLC on a chiral phase (Daicel Chiralpak® AD-H) with acetonitrile yielded the pure enantiomers (−)-trans-2-[6-(4-fluoro-phenyl)-pyridin-3-yl]-cyclopropanecarboxylic acid ethyl ester (enantiomer 1) and (+)-trans-2-[6-(4-fluoro-phenyl)-pyridin-3-yl]-cyclopropanecarboxylic acid ethyl ester (enantiomer 2) one of which is (1R,2R)-2-[6-(4-fluoro-phenyl)-pyridin-3-yl]-cyclopropanecarboxylic acid ethyl ester and the other of which is (1S,2S)-2-[6-(4-fluoro-phenyl)-pyridin-3-yl]-cyclopropanecarboxylic acid ethyl ester.

Enantiomer 1 (Example 54-1): HPLC retention time=6.62 min. MS: m/e=285 (M$^+$).

Enantiomer 2 (Example 54-2): HPLC retention time=8.04 min. MS: m/e=285 (M$^+$).

HPLC conditions: column: Daicel Chiralpak® AD-H, 250×4.6 mm; eluent: acetonitrile; flow rate: 1 ml/min.

Example 55

(1R,2R)-2-[6-(4-Fluoro-phenyl)-pyridin-3-yl]-cyclopropanecarboxylic acid or (1S,2S)-2-[6-(4-fluoro-phenyl)-pyridin-3-yl]-cyclopropanecarboxylic acid

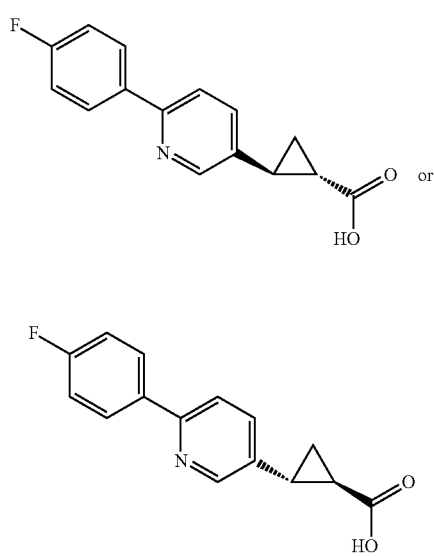

The enantiomerically pure title compound was prepared as described in Example 1(d) by hydrolysis of (−)-trans-2-[6-(4-fluoro-phenyl)-pyridin-3-yl]-cyclopropanecarboxylic acid ethyl ester (Example 54-1).

MS: m/e=258 (M+H)$^+$

Example 56

(1R,2R)-2-[6-(4-Fluoro-phenyl)-pyridin-3-yl]-cyclopropanecarboxylic acid (2,2,2-trifluoro-ethyl)-amide or (1S,2S)-2-[6-(4-fluoro-phenyl)-pyridin-3-yl]-cyclopropanecarboxylic acid (2,2,2-trifluoro-ethyl)-amide

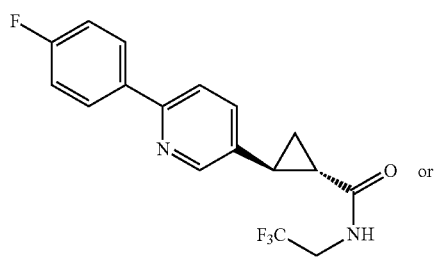

-continued

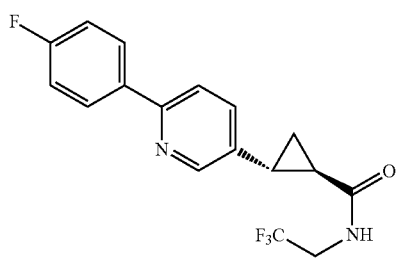

The enantiomerically pure title compound was prepared as described in Example 1(e) and (f) from the compound of Example 55.

MS: m/e=339 (M+H)⁺

Example 57

(1R,2R)-2-[6-(4-Fluoro-phenyl)-pyridin-3-yl]-cyclopropanecarboxylic acid (2,2-difluoro-ethyl)-amide or (1S,2S)-2-[6-(4-fluoro-phenyl)-pyridin-3-yl]-cyclopropanecarboxylic acid (2,2-difluoro-ethyl)-amide

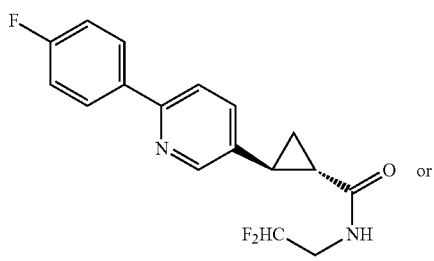

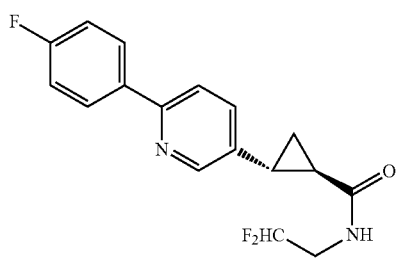

The enantiomerically pure title compound was prepared as described in Example 1(e) and (f) from the compound of Example 55.

MS: m/e=321 (M+H)⁺

Example 58

(1R,2R)-2-[6-(4-Fluoro-phenyl)-pyridin-3-yl]-cyclopropanecarboxylic acid (2-fluoro-ethyl)-amide or (1S,2S)-2-[6-(4-fluoro-phenyl)-pyridin-3-yl]-cyclopropanecarboxylic acid (2-fluoro-ethyl)-amide

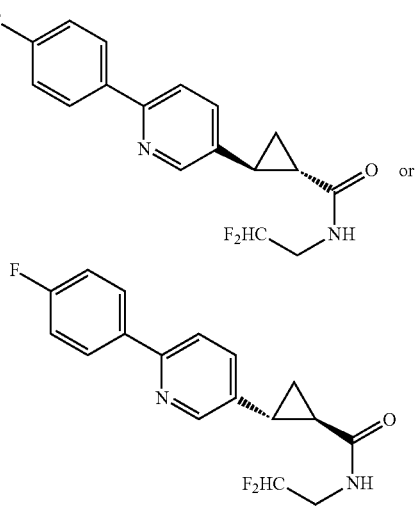

The enantiomerically pure title compound was prepared as described in Example 1(e) and (f) from the compound of Example 55.

MS: m/e=303 (M+H)⁺

Example 59

(Azetidin-1-yl)-{(1R,2R)-2-[6-(4-fluoro-phenyl)-pyridin-3-yl]-cyclopropyl}-methanone or (Azetidin-1-yl)-{(1S,2S)-2-[6-(4-fluoro-phenyl)-pyridin-3-yl]-cyclopropyl}-methanone

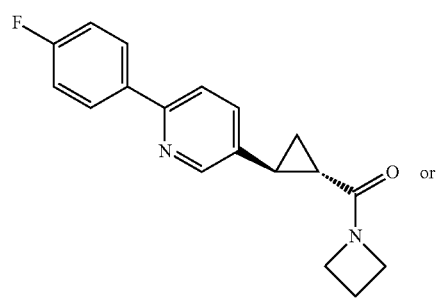

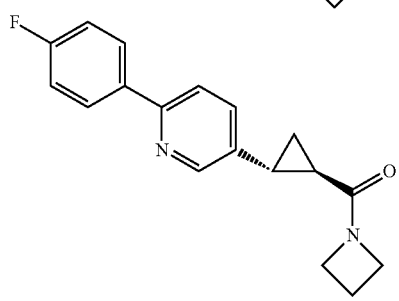

The enantiomerically pure title compound was prepared as described in Example 1(e) and (f) from the compound of Example 55.

MS: m/e=297 (M+H)$^+$

Determination of the Biological Activity

A) Activation of eNOS Transcription

Activation of eNOS transcription was measured as described in detail by Li et al., "Activation of protein kinase C alpha and/or epsilon enhances transcription of the human endothelial nitric oxide synthase gene", Mol. Pharmacol. 53 (1998) 630. Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No. E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

Numerous compounds of the instant invention were tested by the above-described assay and found to increase protein transcription. Generally, the tested compounds exhibited $EC_{50}$ values of less than about 50 µM. Preferred compounds, including the compounds of examples 30, 46, 47, 57, for example, exhibited $EC_{50}$ values of from about 5 µM to about 0.5 µM. More preferred compounds, including the compounds of examples 49, 58, for example, exhibited $EC_{50}$ values of less than about 0.5 µM.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compound incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemofluorescence detection method.

The effect of the compounds of the formulae I and Ia can also be investigated in the following animal models (animal experiments are performed in accordance with the German animal protection law and the guidelines for the use of experimental animals as given by the Guide for the Care and Use of Laboratory Animals of the US National Institutes of Health).

Animals and Treatment (Experiments B-D)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% of fat and 0.001% of cholesterol; in the following designated as placebo group) or a standard rodent chow+test compound (10 or 30 mg/kg/day p.o.).

B) Anti-Hypertensive Effect in ApoE Knockout Mice

Blood-pressure is determined in conscious mice using a computerized tail-cuff system (Visitech Systems, Apex, N.C.). After treatment of ApoE deficient mice and eNOS deficient mice with the test compounds the blood pressure is compared to the results obtained with a placebo treatment.

C) Inhibition of Neointima Formation and Atherogenesis (Femoral Artery Cuff)

After 3 day treatment of ApoE deficient mice with the respective compound (10 mg/kg/day pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al. (J Clin. Invest. 101 (1998) 1225). Briefly, the left femoral artery is dissected. A non-occlusive 2.0 mm polyethylene cuff made of PE 50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

D) Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

E) Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) of 6 month of age and weighing 28 to 36 g are used in the experiments. Mice are divided into 3 groups (C57BL/6J, n=8; apoE control, n=8; apoE with respective compound, n=8) and receive for 8 weeks either a standard rodent chow (containing 4% of fat and 0.001% of cholesterol) or a standard rodent chow+respective compound (30 mg/kg/day p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using spezialized software (HEM, Notocord).

Hearts are allowed to stabilize for 30 min. All functional hemodynamic data are measured during steady state, and during volume and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure and volume loading.

We claim:
1. A compound of the formula I,

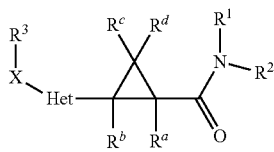

I in which
Het is a 5-membered or 6-membered, monocyclic aromatic group which contains one or two identical or different heteroatom ring members chosen from N, $NR^4$, O and S, and which can be substituted on ring carbon atoms by one or more identical or different substituents $R^5$;
X is chosen from a direct bond, $CH_2$, O and NH, provided that X cannot be O or NH if the group $R^3$—X— is bonded to a ring nitrogen atom of the group Het;
$R^a$, $R^b$, $R^c$ and $R^d$ are independently of each other chosen from hydrogen, fluorine and $(C_1-C_4)$-alkyl;
$R^1$ and $R^2$ are independently of each other chosen from hydrogen, $(C_1-C_6)$-alkyl, $(C_3-C_6)$-alkenyl, $(C_3-C_6)$-alkynyl, $(C_3-C_7)$-cycloalkyl-$C_nH_{2n}$—, phenyl-$C_nH_{2n}$— and heteroaryl-$C_nH_{2n}$—, wherein the groups $(C_1-C_6)$-alkyl, $(C_3-C_7)$-cycloalkyl, $(C_3-C_6)$-alkenyl and $(C_3-C_6)$-alkynyl can all be substituted by one or more identical or different substituents $R^6$, and the groups $C_nH_{2n}$ can all be substituted by one or more identical or different substituents chosen from fluorine and $(C_1-C_4)$-alkyl, and all phenyl and heteroaryl groups can independently of each other be substituted on carbon atoms by one or more identical or different substituents $R^7$,
or $R^1$ and $R^2$, together with the nitrogen atom carrying them, form a 4-membered to 7-membered monocyclic, saturated or unsaturated ring which, in addition to the ring nitrogen atom carrying $R^1$ and $R^2$, can contain one or two further heteroatom ring members chosen from N, $NR^9$, O, S, SO and $SO_2$ which can be identical or different, with the proviso that two ring members from the series O, S, SO and $SO_2$ cannot be present in adjacent ring positions, wherein the ring formed by $R^1$ and $R^2$ together with the nitrogen atom carrying them can be substituted on ring carbon atoms by one or more identical or different substituents $R^8$;
$R^3$ is chosen from phenyl and heteroaryl which can all be substituted by one or more identical or different substituents chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $H_2NSO_2$— and $(C_1-C_4)$-alkyl-$SO_2$—;
$R^4$ is chosen from hydrogen and $(C_1-C_4)$-alkyl;
$R^5$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$ and $(C_1-C_4)$-alkyl-$SO_2$—;
$R^6$ is chosen from fluorine, OH, oxo, $(C_1-C_4)$-alkyloxy, $(C_1-C_4)$-alkylmercapto, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN and $CF_3$;
$R^7$ is chosen from halogen, $(C_1-C_4)$-alkyl, $(C_1-C_4)$-alkyloxy-$(C_1-C_2)$-alkyl-, OH, $(C_1-C_4)$-alkyloxy which can be substituted by one or more fluorine atoms, $(C_1-C_3)$-alkylenedioxy which can be substituted by one or more fluorine atoms, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN, $CF_3$, $SF_5$, $H_2NSO_2$— and $(C_1-C_4)$-alkyl-$SO_2$—;
$R^8$ is chosen from fluorine, $(C_1-C_4)$-alkyl, $(C_1-C_4)$-alkyloxy-$(C_1-C_2)$-alkyl-, OH, oxo, $(C_1-C_4)$-alkyloxy which can be substituted by one or more fluorine atoms, $(C_1-C_3)$-alkylenedioxy, $(C_1-C_4)$-alkylmercapto, $NH_2$, $(C_1-C_4)$-alkylamino, di$((C_1-C_4)$-alkyl)amino, $((C_1-C_4)$-alkyl)-CONH—, di$((C_1-C_4)$-alkyl)aminocarbonyl-, $((C_1-C_4)$-alkyl)aminocarbonyl-, $((C_1-C_4)$-alkyloxy)carbonyl-, $CONH_2$, CN and $CF_3$;
$R^9$ is chosen from hydrogen, $(C_1-C_4)$-alkyl, $((C_1-C_4)$-alkyl)-CO— and phenyl-CO—, wherein the phenyl group can be substituted by one or more identical or different substituents chosen from halogen, $(C_1-C_4)$-alkyl, $CF_3$ and $(C_1-C_4)$-alkyloxy;
$R^{10}$ is chosen from hydrogen and $(C_1-C_4)$-alkyl;
heteroaryl is a 5-membered or 6-membered, monocyclic aromatic group which contains one, two or three identical or different heteroatom ring members chosen from N, $NR^{10}$, O and S; and n is 0, 1 or 2, where all numbers n are independent of each other and can be identical or different;

in any of its stereoisomeric forms or a mixture of stereoisomeric forms in any ratio, or a physiologically acceptable salt thereof.

2. A compound as claimed in claim 1, in which
$R^1$ is chosen from $(C_1-C_4)$-alkyl, $(C_3-C_7)$-cycloalkyl-$C_nH_{2n}$—, phenyl-$C_nH_{2n}$— and heteroaryl-$C_nH_{2n}$—, and $R^2$ is chosen from hydrogen and $(C_1-C_4)$-alkyl, wherein all $(C_1-C_4)$-alkyl and $(C_3-C_7)$-cycloalkyl groups can be substituted by one or more identical or different substituents $R^6$, and all phenyl and heteroaryl groups can be substituted by one or more identical or different substituents $R^7$, or $R^1$ and $R^2$, together with the nitrogen atom carrying them, form a 4-membered to 7-membered monocyclic, saturated ring which, in addition to the ring nitrogen atom carrying $R^1$ and $R^2$, can contain one further heteroatom ring member chosen from $NR^9$, O, S, SO and $SO_2$, wherein the ring formed by $R^1$ and $R^2$ and the nitrogen atom carrying them can be substituted by one or more identical or different substituents $R^8$; or a physiologically acceptable salt thereof.

3. A compound as claimed in claim 1, in which
$R^3$ is chosen from phenyl, pyridinyl and thiophenyl, which can all be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—; or a physiologically acceptable salt thereof.

4. A compound as claimed in claim 3, in which
$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—; or a physiologically acceptable salt thereof.

5. A compound as claimed in claim 1, in which
Het is chosen from pyridinediyl, thiazolediyl, oxazolediyl, imidazolediyl and thiophenediyl, which can all be substituted on ring carbon atoms by one or more identical or different substituents $R^5$ and in which one of the ring nitrogen atoms of the imidazolediyl group carries a group $R^4$; or a physiologically acceptable salt thereof.

6. A compound as claimed in claim 1, in which X is chosen from a direct bond and O; or a physiologically acceptable salt thereof.

7. A compound as claimed in claim 1, in which
Het is chosen from pyridinediyl, thiazolediyl, oxazolediyl, imidazolediyl and thiophenediyl, which can all be substituted on ring carbon atoms by one or more identical or different substituents $R^5$ and in which one of the ring nitrogen atoms of the imidazolediyl group carries a group $R^4$;
X is chosen from a direct bond and O;
$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, di$((C_1-C_4)$-alkyl)amino, $CONH_2$, CN, $CF_3$ and $(C_1-C_4)$-alkyl-$SO_2$—;
or a physiologically acceptable salt thereof.

8. A process for the preparation of a compound as claimed in claim 1, or a physiologically acceptable salt thereof, comprising reacting a compound of the formula IV and a compound of the formula V,

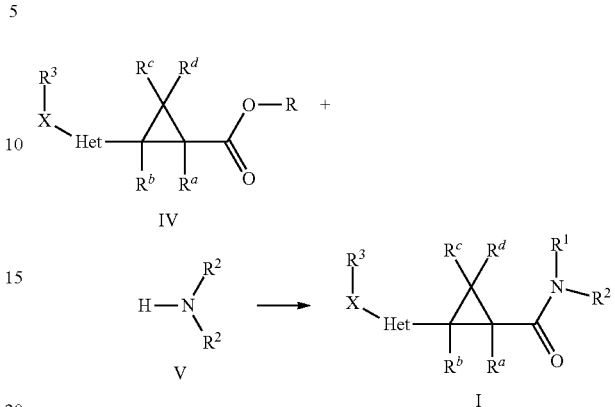

wherein Het, X, $R^a$, $R^b$, $R^c$, $R^d$, $R^1$, $R^2$ and $R^3$ are defined as in claim 1 and, in addition, any functional groups can be present in protected form or in the form of precursor groups, and R is hydrogen, $(C_1-C_4)$-alkyl or benzyl.

9. A pharmaceutical composition, comprising at least one compound as claimed in claim 1, or a physiologically acceptable salt thereof, and a pharmaceutically acceptable carrier.

10. A method of treating a patient for a condition selected from stable or unstable angina pectoris, coronary heart disease, coronary artery disease, Prinzmetal angina, acute coronary syndrome, cardiac insufficiency, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes, diabetes complications, nephropathy, retinopathy, angiogenesis, asthma bronchiale, chronic renal failure, cirrhosis of the liver, osteoporosis, restricted memory performance or a restricted ability to learn, or for the lowering of cardiovascular risk of postmenopausal women or after intake of contraceptives, the method comprising administering to the patient a pharmaceutically effective dose of a compound of the formula Ia,

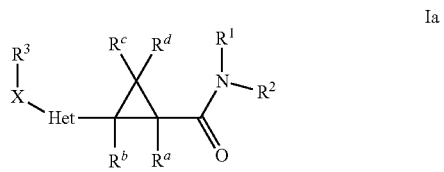

in which
Het is a 5-membered to 10-membered, monocyclic or bicyclic, aromatic group which contains one or more identical or different heteroatom ring members chosen from N, $NR^4$, O and S, and which can be substituted on ring carbon atoms by one or more identical or different substituents $R^5$;
X is chosen from a direct bond, $CH_2$, O, $CH_2$—O, O—$CH_2$, S, NH and $N((C_1-C_4)$-alkyl), or X is absent and in this case the phenyl, naphthalenyl or heteroaryl group representing the group $R^3$ is fused to the group Het, provided that X cannot be O, CH$_2$—O, S, NH or N(($C_1$-$C_4$)-alkyl) if the group R$^3$—X— is bonded to a ring nitrogen atom of the group Het;

R$^a$, R$^b$, R$^c$ and R$^d$ are independently of each other chosen from hydrogen, fluorine and ($C_1$-$C_4$)-alkyl;

R$^1$ and R$^2$ are independently of each other chosen from hydrogen, ($C_1$-$C_{10}$)-alkyl, ($C_3$-$C_{10}$)-alkenyl, ($C_3$-$C_{10}$)-alkynyl, ($C_3$-$C_{10}$)-cycloalkyl-$C_nH_{2n}$—, phenyl-$C_nH_{2n}$—, naphthalenyl-$C_nH_{2n}$— and heteroaryl-$C_nH_{2n}$—, wherein the groups ($C_1$-$C_{10}$)-alkyl, ($C_3$-$C_{10}$)-cycloalkyl, ($C_3$-$C_{10}$)-alkenyl and ($C_3$-$C_{10}$)-alkynyl can all be substituted by one or more identical or different substituents R$^6$, and the groups $C_nH_{2n}$ can all be substituted by one or more identical or different substituents chosen from fluorine and ($C_1$-$C_4$)-alkyl, and all phenyl, naphthalenyl and heteroaryl groups can independently of each other be substituted by one or more identical or different substituents R$^7$, or R$^1$ and R$^2$, together with the nitrogen atom carrying them, form a 4-membered to 10-membered, monocyclic or bicyclic, saturated or unsaturated ring which, in addition to the ring nitrogen atom carrying R$^1$ and R$^2$, can contain one or two further heteroatom ring members chosen from N, NR$^9$, O, S, SO and SO$_2$ which can be identical or different, with the proviso that two ring members from the series O, S, SO and SO$_2$ cannot be present in adjacent ring positions, wherein the ring formed by R$^1$ and R$^2$ together with the nitrogen atom carrying them can be substituted by one or more identical or different substituents R$^8$;

R$^3$ is chosen from phenyl, naphthalenyl and heteroaryl which can all be substituted by one or more identical or different substituents chosen from halogen, ($C_1$-$C_6$)-alkyl, ($C_1$-$C_6$)-alkyloxy-($C_1$-$C_3$)-alkyl-, OH, ($C_1$-$C_6$)-alkyloxy which can be substituted by one or more fluorine atoms, ($C_1$-$C_3$)-alkylenedioxy which can be substituted by one or more fluorine atoms, ($C_1$-$C_6$)-alkylmercapto, NH$_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-SO$_2$NH—, di(($C_1$-$C_6$)-alkyl)aminocarbonyl-, (($C_1$-$C_6$)-alkyl)aminocarbonyl-, (($C_1$-$C_6$)-alkyloxy)carbonyl-, COOH, CONH$_2$, CN, CF$_3$, (($C_1$-$C_6$)-alkyl)NHSO$_2$—, di(($C_1$-$C_6$)-alkyl)NSO$_2$—, H$_2$NSO$_2$— and ($C_1$-$C_6$)-alkyl-SO$_2$—;

R$^4$ is chosen from hydrogen and ($C_1$-$C_4$)-alkyl;

R$^5$ is chosen from halogen, ($C_1$-$C_6$)-alkyl, ($C_1$-$C_6$)-alkyloxy-($C_1$-$C_3$)-alkyl-, OH, ($C_1$-$C_6$)-alkyloxy which can be substituted by one or more fluorine atoms, ($C_1$-$C_6$)-alkylmercapto, NH$_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-SO$_2$NH—, di(($C_1$-$C_6$)-alkyl)aminocarbonyl-, (($C_1$-$C_6$)-alkyl)aminocarbonyl-, (($C_1$-$C_6$)-alkyloxy)carbonyl-, COOH, CONH$_2$, CN, CF$_3$, H$_2$NSO$_2$—, (($C_1$-$C_6$)-alkyl)NHSO$_2$—, di(($C_1$-$C_6$)-alkyl)NSO$_2$— and ($C_1$-$C_6$)-alkyl-SO$_2$—;

R$^6$ is chosen from fluorine, OH, oxo, ($C_1$-$C_6$)-alkyloxy, ($C_1$-$C_6$)-alkylmercapto, di(($C_1$-$C_6$)-alkyl)amino, (($C_1$-$C_6$)-alkyl)-CONH—, (($C_1$-$C_6$)-alkyl)-SO$_2$NH—, di(($C_1$-$C_6$)-alkyl)aminocarbonyl-, (($C_1$-$C_6$)-alkyl)aminocarbonyl-, (($C_1$-$C_6$)-alkyloxy)carbonyl-, CONH$_2$, CN and CF$_3$;

R$^7$ is chosen from halogen, ($C_1$-$C_6$)-alkyl, ($C_1$-$C_6$)-alkyloxy-($C_1$-$C_3$)-alkyl-, OH, ($C_1$-$C_6$)-alkyloxy which can be substituted by one or more fluorine atoms, ($C_1$-$C_3$)-alkylenedioxy which can be substituted by one or more fluorine atoms, ($C_1$-$C_6$)-alkylmercapto, NH$_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-SO$_2$NH—, di(($C_1$-$C_6$)-alkyl)aminocarbonyl-, (($C_1$-$C_6$)-alkyl)aminocarbonyl-, (($C_1$-$C_6$)-alkyloxy)carbonyl-, CONH$_2$, CN, CF$_3$, SF$_5$, H$_2$NSO$_2$—, (($C_1$-$C_6$)-alkyl)NHSO$_2$—, di(($C_1$-$C_6$)-alkyl)NSO$_2$— and ($C_1$-$C_6$)-alkyl-SO$_2$—;

R$^8$ is chosen from halogen, ($C_1$-$C_6$)-alkyl, ($C_1$-$C_6$)-alkyloxy-($C_1$-$C_3$)-alkyl-, OH, oxo, ($C_1$-$C_6$)-alkyloxy which can be substituted by one or more fluorine atoms, ($C_1$-$C_3$)-alkylenedioxy which can be substituted by one or more fluorine atoms, ($C_1$-$C_6$)-alkylmercapto, NH$_2$, ($C_1$-$C_6$)-alkylamino, di(($C_1$-$C_6$)-alkyl)amino, (($C_1$-$C_6$)-alkyl)-CONH—, (($C_1$-$C_6$)-alkyl)-SO$_2$NH—, di(($C_1$-$C_6$)-alkyl)aminocarbonyl-, (($C_1$-$C_6$)-alkyl)aminocarbonyl-, (($C_1$-$C_6$)-alkyloxy)carbonyl-, CONH$_2$, CN, CF$_3$, H$_2$NSO$_2$—, (($C_1$-$C_6$)-alkyl)NHSO$_2$—, di(($C_1$-$C_6$)-alkyl)NSO$_2$— and ($C_1$-$C_6$)-alkyl-SO$_2$—;

R$^9$ is chosen from hydrogen, ($C_1$-$C_6$)-alkyl, (($C_1$-$C_6$)-alkyl)-CO— and phenyl-CO—, wherein the phenyl group can be substituted by one or more identical or different substituents chosen from halogen, ($C_1$-$C_4$)-alkyl, CF$_3$ and ($C_1$-$C_4$)-alkyloxy;

R$^{10}$ is chosen from hydrogen and ($C_1$-$C_4$)-alkyl;

heteroaryl is a 5-membered to 10-membered, monocyclic or bicyclic aromatic group which contains one or more identical or different heteroatom ring members chosen from N, NR$^{10}$, O and S; and n is 0, 1, 2 or 3, where all numbers n are independent of each other and can be identical or different;

in any of its stereoisomeric forms or a mixture of stereoisomeric forms in any ratio, or a physiologically acceptable salt thereof.

11. A method of treating a patient for a condition selected from stable or unstable angina pectoris, coronary heart disease, coronary artery disease, Prinzmetal angina, acute coronary syndrome, cardiac insufficiency, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes, diabetes complications, nephropathy, retinopathy, angiogenesis, asthma bronchiale, chronic renal failure, cirrhosis of the liver, osteoporosis, restricted memory performance or a restricted ability to learn, or for the lowering of cardiovascular risk of postmenopausal women or after intake of contraceptives, the method comprising administering to the patient a pharmaceutically effective dose of a compound of the formula I as defined in claim 1, or a physiologically acceptable salt thereof.

12. The method as claimed in claim 11, wherein in the compound of the formula I, R$^3$ is phenyl which can be substituted by one or more identical or different substituents chosen from halogen, ($C_1$-$C_4$)-alkyl, ($C_1$-$C_4$)-alkyloxy-($C_1$-$C_2$)-alkyl-, ($C_1$-$C_4$)-alkyloxy which can be substituted by one or more fluorine atoms, $(C_1-C_4)$-alkylmercapto, $(C_1-C_4)$-alkylamino, $di((C_1-C_4)$-alkyl)amino, $CONH_2$, CN, $CF_3$ and $(C_1-C_4)$-alkyl-$SO_2$—.

13. The method as claimed in claim 11, wherein in the compound of the formula I, Het is chosen from pyridinediyl, thiazolediyl, oxazolediyl, imidazolediyl and thiophenediyl, which can all be substituted on ring carbon atoms by one or more identical or different substituents $R^5$ and in which one of the ring nitrogen atoms of the imidazolediyl group carries a group $R^4$;

X is chosen from a direct bond and O;

$R^3$ is phenyl which can be substituted by one or more identical or different substituents chosen from halogen, $(C_1-C_4)$-alkyl, $(C_1-C_4)$-alkyloxy-$(C_1-C_2)$-alkyl-, $(C_1-C_4)$-alkyloxy which can be substituted by one or more fluorine atoms, $(C_1-C_4)$-alkylmercapto, $(C_1-C_4)$-alkylamino, $di((C_1-C_4)$-alkyl)amino, $CONH_2$, CN, $CF_3$ and $(C_1-C_4)$-alkyl-$SO_2$—.

* * * * *